(12) United States Patent
Honda et al.

(10) Patent No.: US 12,083,357 B2
(45) Date of Patent: Sep. 10, 2024

(54) RADIATION THERAPY APPARATUS AND CONTROL METHOD OF RADIATION THERAPY APPARATUS

(71) Applicant: Hitachi High-Tech Corporation, Tokyo (JP)

(72) Inventors: Taizo Honda, Tokyo (JP); Tatsuya Fujisawa, Tokyo (JP); Chihiro Nakashima, Tokyo (JP); Tomokazu Shimakura, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 100 days.

(21) Appl. No.: 17/272,705

(22) PCT Filed: Oct. 24, 2019

(86) PCT No.: PCT/JP2019/041676
§ 371 (c)(1),
(2) Date: Mar. 2, 2021

(87) PCT Pub. No.: WO2020/174745
PCT Pub. Date: Sep. 3, 2020

(65) Prior Publication Data
US 2021/0370094 A1 Dec. 2, 2021

(30) Foreign Application Priority Data
Feb. 25, 2019 (JP) .................. 2019-031587

(51) Int. Cl.
*A61N 5/10* (2006.01)

(52) U.S. Cl.
CPC ......... *A61N 5/1037* (2013.01); *A61N 5/1039* (2013.01); *A61N 5/1048* (2013.01); *A61N 5/1081* (2013.01)

(58) Field of Classification Search
CPC ...... A61N 5/01; A61N 5/1037; A61N 5/1039; A61N 5/1048; A61N 5/1075;
(Continued)

(56) References Cited

U.S. PATENT DOCUMENTS

| | | | | |
|---|---|---|---|---|
| 2001/0001807 A1* | 5/2001 | Green | ................ | G01R 33/4808 378/65 |
| 2004/0024300 A1* | 2/2004 | Graf | ..................... | A61N 5/1049 600/407 |

(Continued)

FOREIGN PATENT DOCUMENTS

| | | | |
|---|---|---|---|
| JP | 2014-138671 A | | 7/2014 |
| JP | 2016129639 A | * | 7/2016 |

(Continued)

OTHER PUBLICATIONS

Extended European Search Report received in corresponding European Application No. 19916925.1 dated Sep. 21, 2022.
(Continued)

*Primary Examiner* — Christine H Matthews
*Assistant Examiner* — Marc D. Honrath
(74) *Attorney, Agent, or Firm* — MATTINGLY & MALUR, PC

(57) ABSTRACT

A radiation therapy apparatus that enhances the reliability and ease of use of a treatment is provided. A radiation therapy apparatus includes: a treatment bed moving a top plate with an object to be treated placed on the top plate to a predetermined treatment location; an imaging apparatus moving to the predetermined treatment location from a direction different from the direction of movement of the top plate and picking up an image of the object to be treated; and an irradiation apparatus provided between the treatment bed and the imaging apparatus, extensible, and applying a radioactive ray to the object to be treated. When the CT apparatus (Continued)

moves to the treatment location, the irradiation apparatus moves to a predetermined waiting position. When applying a radioactive ray to an object to be treated, the irradiation apparatus moves to a predetermined irradiation position.

12 Claims, 14 Drawing Sheets

(58) Field of Classification Search
CPC .......... A61N 5/1081; A61N 2005/1055; A61N 2005/1061; A61N 2005/1063; A61N 2005/1087
See application file for complete search history.

(56) References Cited

U.S. PATENT DOCUMENTS

| | | | |
|---|---|---|---|
| 2011/0182411 A1* | 7/2011 | Shinagawa | A61N 5/10 378/65 |
| 2012/0035470 A1* | 2/2012 | Kuduvalli | A61B 6/00 600/427 |
| 2012/0189102 A1 | 7/2012 | Maurer, Jr. et al. | |
| 2014/0228615 A1* | 8/2014 | Ikeda | A61N 5/1081 600/1 |
| 2017/0001041 A1 | 1/2017 | Yamashita et al. | |
| 2017/0273643 A1* | 9/2017 | Maurer, Jr. | A61N 5/1081 |
| 2017/0340903 A1* | 11/2017 | Ie | A61B 6/4452 |
| 2018/0345043 A1* | 12/2018 | Kinugasa | A61N 5/1081 |

FOREIGN PATENT DOCUMENTS

| | | | |
|---|---|---|---|
| JP | 2017-012374 A | 1/2017 | |
| JP | 2018-148937 A | 9/2018 | |
| JP | 2018-199074 A | 12/2018 | |
| WO | WO-03008986 A2 * | 1/2003 | .............. A61B 5/055 |
| WO | 2007/060242 A1 | 5/2007 | |

OTHER PUBLICATIONS

International Search Report of PCT/JP2019/041676 dated Dec. 3, 2019.

* cited by examiner

RADIATION THERAPY APPARATUS AND CONTROL METHOD OF RADIATION THERAPY APPARATUS

TECHNICAL FIELD

The present invention relates to a radiation therapy apparatus and a control method of a radiation therapy apparatus.

BACKGROUND ART

Radiation therapy is a therapy in which, for example, a gamma ray, an X ray, or a particle ray is applied to an affected part to destroy cancer cells (Patent Publication 1). The particle rays include, for example, neutron ray, proton (hydrogen) beam, helium line, carbon ion beam, and the like.

In recent years, to enhance the reliability of radiation therapy and reduce the burdens on patients, there is demand for adaptive therapies in which a treatment plan is modified according to change in the size of a tumor and change in the physique of a patient. In adaptive therapies, for example, a CT (Computed Tomography) image is acquired immediately before a treatment and a treatment plan is modified based on the acquired image. To implement an adaptive therapy at this time, a highly accurate CT image must be acquired at an isocenter where a treatment is given.

When an CT image is picked up at an isocenter, interference between an irradiation apparatus applying a radioactive ray and a CT apparatus must be avoided. To avoid interference between a CT apparatus and an irradiation apparatus during imaging, the irradiation apparatus could be installed outside the CT apparatus. In this case, a distance between the irradiation apparatus and an isocenter is lengthened. In case of particle ray therapy, a distance by which a particle ray going out of a vacuumed irradiation apparatus travels in the air is increased with increase in a distance between the irradiation apparatus and an isocenter; and a beam size is increased due to scattering by the air. As a result, the quality and controllability of dose distribution are degraded.

Consequently, to share one treatment bed between a CT apparatus and a radiation irradiation apparatus, a technology is proposed. In this technology, at a time of imaging with the CT apparatus, an arm portion of the radiation therapy apparatus is moved up to prevent interference between the CT apparatus and the radiation therapy apparatus; and after imaging, a treatment with a radioactive ray is performed (Patent Publication 2).

RELATED ART DOCUMENTS

Patent Publications

[Patent Publication 1] Japanese Unexamined Patent Application Publication No. 2017-12374

[Patent Publication 2] Japanese Unexamined Patent Application Publication No. 2014-138671

SUMMARY OF THE INVENTION

Problems to be Solved by the Invention

In the technology disclosed in Patent Publication 2, a top plate of a bet apparatus is provided through a CT apparatus; and thus, the movement of the top plate is restricted. According to this conventional art, therefore, ease of use for a patient getting on or off the top plate is degraded and the position or angle of the top plate is difficult to change according to a treatment plan.

In consideration of the above problems, the present invention has been made and it is an object of the present invention to provide a radiation therapy apparatus, a radiation therapy method, and a method for creating a treatment plan for a radiation therapy apparatus in which the reliability and ease of use of a treatment can be enhanced.

Means of Solving the Problems

To solve the above problems, a radiation therapy apparatus according to the present invention is a radiation therapy apparatus including: a treatment bed moving a top plate with an object to be treated placed thereon to a predetermined treatment location; an imaging apparatus moving to the predetermined treatment location from a direction different from the direction of movement of the top plate and picking up an image of the object to be treated; and an irradiation apparatus provided between the treatment bed and the imaging apparatus, extensible, and applying a radioactive ray to the object to be treated. The irradiation apparatus retracts to a predetermined waiting position when the imaging apparatus moves to the predetermined treatment location and moves to a predetermined irradiation position when applying a radioactive ray to the object to be treated.

Effects of the Invention

According to the present invention, imaging and treatment can be performed without moving an object to be treated on the top plate and a highly precise treatment can be performed. According to the present invention, further, the treatment bed movable to a predetermined treatment location is provided; therefore, ease of use can be enhanced in getting an object to be treated onto and off the top plate.

BEST MODE FOR CARRYING OUT THE INVENTION

Hereafter, a description will be given to embodiments of the present invention with reference to the drawings. In the description of the embodiments, a particle ray therapy apparatus applying a particle ray will be taken as an example of a radiation therapy apparatus. The present embodiments are applicable not only to a particle ray but also to an X ray or an electron beam. In the following description, a particle ray may be expressed as an ion beam or a beam. In the description of the present embodiments, a CT apparatus will be taken as an example of an imaging apparatus. However, the imaging apparatus is not limited to a CT apparatus and the present embodiments are also applicable to any other imaging apparatus, such as an MRI (Magnetic Resonance Imaging) apparatus and an X-ray imaging apparatus.

Figure 1:
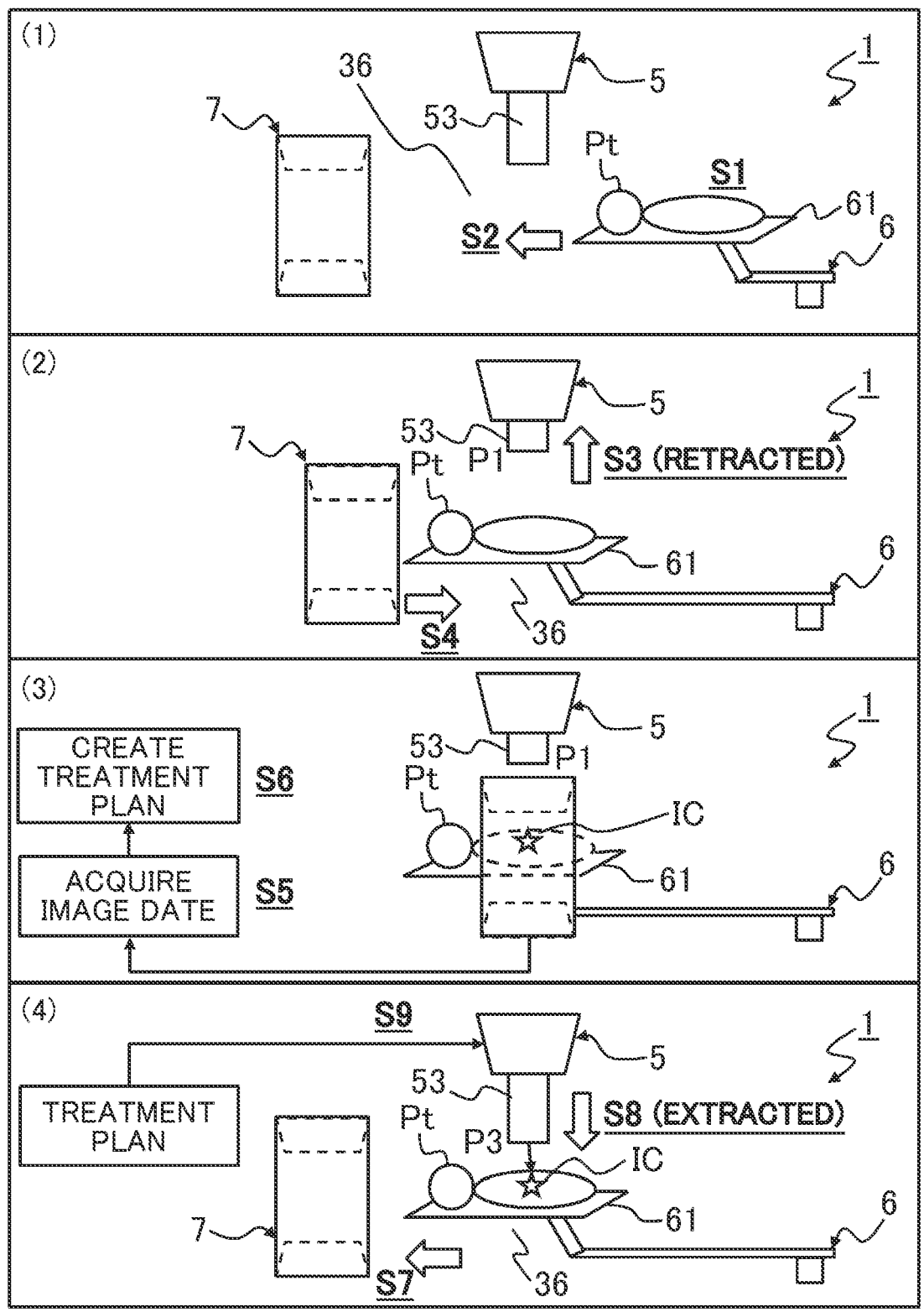
FIG. 1 is an explanatory drawing illustrating an overview of a particle ray therapy apparatus.

FIG. 1 illustrates an overview of a particle ray therapy apparatus as a radiation therapy apparatus. The details of the configuration of the apparatus will be described later with reference to FIG. 2 and the following drawings.

As illustrated in FIG. 1, the particle ray therapy apparatus 1 includes, for example, an irradiation apparatus 5, a treatment bed 6, and a CT apparatus 7 as an "imaging apparatus."

In the initial stage shown in FIG. 1(1), a patient Pt is secured on a top plate 61 of the treatment bed 6 (S1) and then, the top plate 61 is moved to an irradiation chamber 36 as a "predetermined treatment location" (S2). "Predetermined treatment location" cited here refers to a location where an affected part of a patient Pt is settled in a position and a direction predetermined in a treatment plan and is also a location where the affected part of the patient Pt and an isocenter IC agree with each other. The irradiation chamber 36 is a space in which a particle ray is applied from the irradiation apparatus 5 and a particle ray therapy is performed.

In the CT imaging preparation stage shown in FIG. 1(2), when the CT apparatus 7 is moved, the tip of an irradiation nozzle 53 of the irradiation apparatus 5 is retracted to a predetermined waiting position P1 (S3). After the irradiation nozzle 53 is moved to the waiting position P1, the CT apparatus 7 is moved to the irradiation chamber 36 (S4). The movement of the irradiation nozzle 53 to the waiting position P1 and the movement of the CT apparatus 7 may be simultaneously performed as long as contact between the irradiation nozzle 53 and the CT apparatus 7 can be prevented. When the irradiation nozzle 53 has been retracted to the waiting position prior to the initial stage shown in FIG. 1(1), the irradiation nozzle 53 need not be retracted in the CT imaging preparation stage. The moved CT apparatus 7 stops moving at a location where an image of an affected part of the patient Pt can be picked up, that is, a location where an isocenter IC of the particle ray therapy apparatus comes within a photographing range of the CT apparatus 7.

In the CT imaging stage shown in FIG. 1(3), a cross-sectional image of the vicinity of an isocenter IC set in the affected part of the patient Pt is picked up with the CT apparatus 7 to acquire image data (S5). Based on the acquired image data, a treatment plan indicating where and to what extent a particle ray should be applied is modified or created (S6).

In the treatment stage (irradiation stage) shown in FIG. 1(4), the CT apparatus 7 is retracted from the irradiation chamber 36 to the original standby location (S7) and then, the irradiation apparatus 5 extends the tip of the irradiation nozzle 53 from the waiting position P1 to an irradiation position P3 (S8). The movement of the CT apparatus 7 and the movement of the irradiation nozzle 53 to the irradiation position P3 may be simultaneously performed as long as contact between the irradiation nozzle 53 and the CT apparatus 7 can be prevented. Then, the irradiation apparatus 5 applies a particle ray to the affected part of the patient Pt in accordance with the created treatment plan (S9). FIG. 1(4) illustrates a case where the tip of the irradiation nozzle 53 is brought most closely to the isocenter IC. The present invention is not limited to this and the tip of the irradiation nozzle 53 may be moved to a position where a particle ray is applied while tracking the movement of the affected part as described later with reference to FIG. 5.

According to the thus configured present embodiments, the treatment bed 6 is capable of moving the top plate 61 toward the irradiation chamber 36; the CT apparatus 7 is capable of moving to the irradiation chamber 36 from a direction opposite the direction of movement of the top plate 61; and the irradiation apparatus 5 is capable of extending or retracting the irradiation nozzle 53 according to whether to perform imaging or particle ray treatment.

According to the present embodiments, the CT apparatus 7 is capable of readily accessing the top plate 61 and picking up an image of the vicinity of an isocenter IC. A more specific description will be given. At a time of imaging with the CT apparatus 7, the tip of the irradiation nozzle 53 is retracted to the waiting position P1. Therefore, the CT apparatus 7 is capable of approaching the top plate 61 without interference with the irradiation apparatus 5 and picking up a cross-sectional image of the vicinity of the isocenter IC. When the top plate 61 is moved after a patient Pt is secured on the top plate 61, tissues of the patient Pt would be displaced due to force applied by acceleration or deceleration of the top plate 61. According to the present embodiments, on the other hand, the top plate 61 with a patient Pt placed thereon need not be moved after entry to the irradiation chamber 36 and the position of the top plate can be maintained from CT imaging to particle ray treatment.

According to the present embodiments, high-quality diagnostic image data of the vicinity of an isocenter IC of a patient Pt in the same state as in particle ray treatment can be acquired from the CT apparatus 7 and a treatment plan can be modified or created based on the high-quality diagnostic image data. The reliability of a particle ray therapy can be enhanced by applying a particle ray based on the thus modified or created treatment plan.

According to the present embodiments, further, during a particle ray treatment, the irradiation nozzle 53 is extended to move the tip of the irradiation nozzle 53 from the waiting position P1 to the irradiation position P3; therefore, the irradiation nozzle 53 and an isocenter IC can be brought close to each other. In the present embodiments, as a result, a diameter of a particle ray applied from the irradiation apparatus 5 to an affected part (isocenter) can be reduced in size and the quality of dose distribution can be enhanced.

According to the present embodiments, in addition, the top plate 61 of the treatment bed 6 and the CT apparatus 7 are mechanically separated from each other; therefore, the top plate 61 can enter or exit from the irradiation chamber 36 and an angle of the top plate can be changed without restriction of the structure of the CT apparatus 7. FIG. 1 illustrates a case where the top plate 61 is horizontally held but the top plate can take any other angle than a level.

First Embodiment

Figure 2:
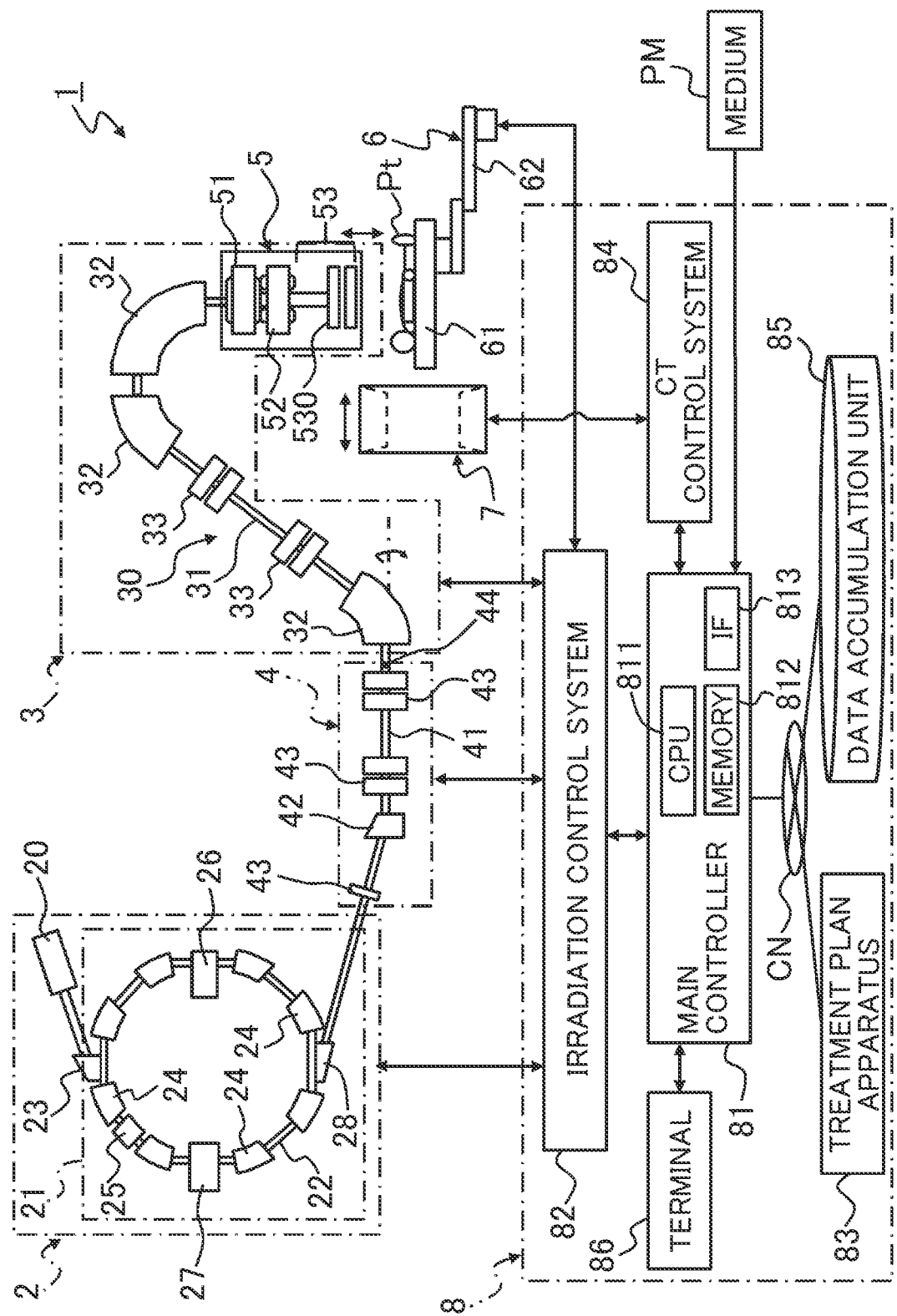
FIG. 2 is an overall block diagram of a particle ray therapy apparatus.

A description will be given to First Embodiment with reference to FIG. 2 to FIG. 9. FIG. 2 illustrates an overall configuration of a particle ray therapy apparatus 1. The particle ray therapy apparatus 1 is installed in a building, not shown. The particle ray therapy apparatus 1 includes, for example, a particle ray generation apparatus 2, a rotary gantry 3, a beam transport system 4, a treatment bed 6, a CT apparatus 7, and an information processing system 8.

The particle ray generation apparatus 2 is an apparatus generating a particle ray as an example of a particle ray of a kind of radioactive ray. The particle ray generation apparatus 2 includes, for example, an ion source, not shown, a linear accelerator 20 as a preaccelerator, and a synchrotron accelerator 21. This embodiment uses a system having the linear accelerator 20 and the synchrotron 21 but the present invention is not limited to this. For example, a cyclotron or a synchro-cyclotron may be used or a particle ray accelerator using a superconducting electromagnet may be used. The particle rays include, for example, proton beam (proton ion beam), helium line (helium ion beam), carbon line (carbon ion beam), and the like. Any of these rays may be adopted.

The synchrotron accelerator 21 includes, for example, an annular beam duct 22, an injector 23, a plurality of bending magnets 24, a plurality of quadrupole magnets 25, a high frequency acceleration cavity 26, a high frequency applying apparatus 27 for emission, and a septum magnet 28 for emission.

The beam duct 22 constitutes a traveling track of a particle ray. The injector 23 attached to the beam duct 22 is connected to the linear accelerator 20 through a vacuum duct. The ion source, not shown, is connected to the linear accelerator 20. The high frequency applying apparatus 27 includes, for example, a high frequency electrode for emission, a high frequency power source, and a switch (none of which is shown). Each bending magnet 24 and each quadrupole magnet 25, the high frequency acceleration cavity 26, and the septum magnet 28 are arranged along the beam duct 22 as shown in FIG. 2.

The beam transport system is roughly divided into a first beam transport system (high-energy beam transport system) 4 transporting a beam from the accelerator 21 to the rotary gantry 3 and a second beam transport system (gantry beam transport system) 30 transporting a beam to the irradiation apparatus 5 in the rotary gantry 3.

The first beam transport system 4 has a beam path (beam duct) 41 connected to the septum magnet 28 of the synchrotron accelerator 21. A plurality of quadrupole magnets 43, a bending magnet 42, and a plurality of quadrupole magnets 43 are arranged from the synchrotron accelerator 21 toward the irradiation apparatus 5 along the beam path 41.

The second beam transport system 30 has a beam path (beam duct) 31. A plurality of bending magnets 32 and a plurality of quadrupole magnets 33 are arranged from the synchrotron accelerator 21 toward the irradiation apparatus 5 along the beam path 31.

The beam path 31 and each electromagnet 32, 33 are attached to the rotary gantry 3. The beam path 31 is in communication with the beam path 41 at a connection 44 between the first beam transport system 4 and the second beam transport system 30. Since the beam path 31 is rotated in conjunction with rotation of the rotary gantry 3, the beam path 31 is not connected directly with the beam path 41 but connected through the connection 44.

The irradiation apparatus 5 applies a particle ray to an affected part of a patient Pt placed on the top plate 61 of the treatment bed 6 from the extensible irradiation nozzle 53 based on a treatment plan. The irradiation apparatus 5 includes, for example, a scanning electromagnet (beam scanning apparatus) 51 in a Y direction, a scanning electromagnet 52 in an X direction X, and an irradiation nozzle 53.

The Y-direction scanning electromagnet 51 deflects a particle ray (beam) within a plane perpendicular to the central axis of the irradiation apparatus 5 and scans in the Y direction. The X-direction scanning electromagnet 52 deflects a particle ray within the plane and scans in the Y direction orthogonal to the X direction. More than one X-direction scanning electromagnet 51 may be provided as described later.

As mentioned above, on the tip side of the irradiation apparatus 5, the irradiation nozzle 53 is provided such that the irradiation nozzle is extensible in the axial direction of the nozzle. The irradiation nozzle 53 includes, for example, a bellows pipe 531, a window 532, a dose monitor 533, 534, a beam position monitor 535, and a ridge filter 536 (Refer to FIG. 4 for any of these items). The window 532 is a boundary between a vacuum and the air. The area from the beam ducts 22, 31, 41 to the window 532 of the irradiation apparatus 5 is kept in a vacuum and a particle ray is accelerated and transported in a vacuum. A particle ray that passed through the window 532 travels in the air.

The irradiation apparatus 5 is mounted on the rotary gantry 3. The irradiation apparatus 5 is so designed that the irradiation apparatus can be moved through, for example, 360° about the rotation axis AX (Refer to FIG. 3) of the rotary gantry 3 by the rotary gantry 3. The irradiation apparatus 5 is positioned at an end of the second beam transport system 30 and the scanning electromagnets 51, 52 and a tip portion 530 are arranged toward a particle ray outlet of the irradiation apparatus 5 along the central axis of the irradiation apparatus 5. The tip portion 530 includes, for example, instruments, such as the dose monitors 533, 534, the beam position monitor 535, the ridge filter 536, a range shifter (not shown), a collimator (not shown), and the like, that monitor and adjust particle rays.

The treatment bed 6 is an apparatus holding a patient Pt in position at a predetermined angle and includes the top plate 61 for placing a patient Pt and a moving mechanism 62. The moving mechanism 62 may be configured, for example, as a robot arm moving the top plate 61 in a plurality of directions (for example, six-axis directions) or may be configured as a mechanism horizontally moving the top plate 61 on a rail.

The CT apparatus 7 is provided opposite to the treatment bed 6 with a space (irradiation chamber 36) that can be irradiated by the irradiation apparatus 5 in between. The CT apparatus 7 is so provided that the CT apparatus can enter or exit from the irradiation chamber 36 from a direction opposite a direction in which the top plate 61 enters the irradiation chamber 36.

The information processing system 8 is a system exercising control of the particle ray therapy apparatus 1 and performing other like operations. The information processing system 8 includes, for example, a main controller 81, an irradiation control system 82, a treatment plan apparatus 83, a CT control system 84, a data accumulation unit 85, and an operation terminal 86. In this example, the main controller

81, the irradiation control system 82, the treatment plan apparatus 83, the CT control system 84, the data accumulation unit 85, and the operation terminal 86 are individually configured as a single system or apparatus. Instead, a plurality of systems or a plurality of apparatuses may be configured as a single system or apparatus or a single system or apparatus may be functionally divided and configured as a plurality of systems or a plurality of apparatuses.

The main controller 81 is a computer controlling the overall operation of the particle ray therapy apparatus 1 and includes such computer resources as a microprocessor 811, a memory 812, and an interface unit 813, for example. In the drawing, the microprocessor 811 is indicated by "CPU" and the interface unit 813 is indicated by "IF." The memory 812 holds a predetermined computer program (not shown) used for controlling the particle ray therapy apparatus 1.

The microprocessor 811 reads a predetermined computer program from the memory 812 and executes the program to control the particle ray therapy apparatus 1. The interface unit 813 includes, for example, a communication interface circuit conforming to one or more communication protocols, an input/output interface circuit, and the like.

The interface unit 813 allows a storage medium PM to be connected. The storage medium PM is configured as, for example, a flash memory, an optical disk, a memory card, a hard disk, or the like. Part or all of a predetermined computer program can be transferred from a storage medium PM to the memory 812 of the main controller 81 and stored there. Conversely, part or all of a predetermined computer program can also be transferred from the memory 812 of the main controller 81 to a storage medium PM and stored there.

The irradiation control system 82 is a computer controlling the entire irradiation of a particle ray by the particle ray therapy apparatus 1. Each of the computers 83, 84, 86 described later, including the irradiation control system 82 has such computer resources as a microprocessor, a memory (neither of which is shown), and the like as the main controller 81 does.

The treatment plan apparatus 83 is a computer creating a plan for performing a treatment by particle ray irradiation. The treatment plan apparatus 83 creates a treatment plan based on the direction of a doctor and image data obtained from the CT apparatus 7.

The CT control system 84 is a computer controlling the operation of the CT apparatus 7. Image data (diagnostic image data) of an affected part obtained by imaging with the CT apparatus 7 is stored into the data accumulation unit 85 via the CT control system 84.

The data accumulation unit 85 stores, for example, image data obtained through imaging with the CT apparatus 7 and a treatment plan created at the treatment plan apparatus 83.

The operation terminal 86 is a computer used by such a user as a medical technologist, a doctor, or the like. A user operates the particle ray therapy apparatus 1 using the operation terminal 86. Further, a user can also acquire information in the particle ray therapy apparatus 1 via the operation terminal 86 and check the information on the screen of the terminal 86.

Figure 3:
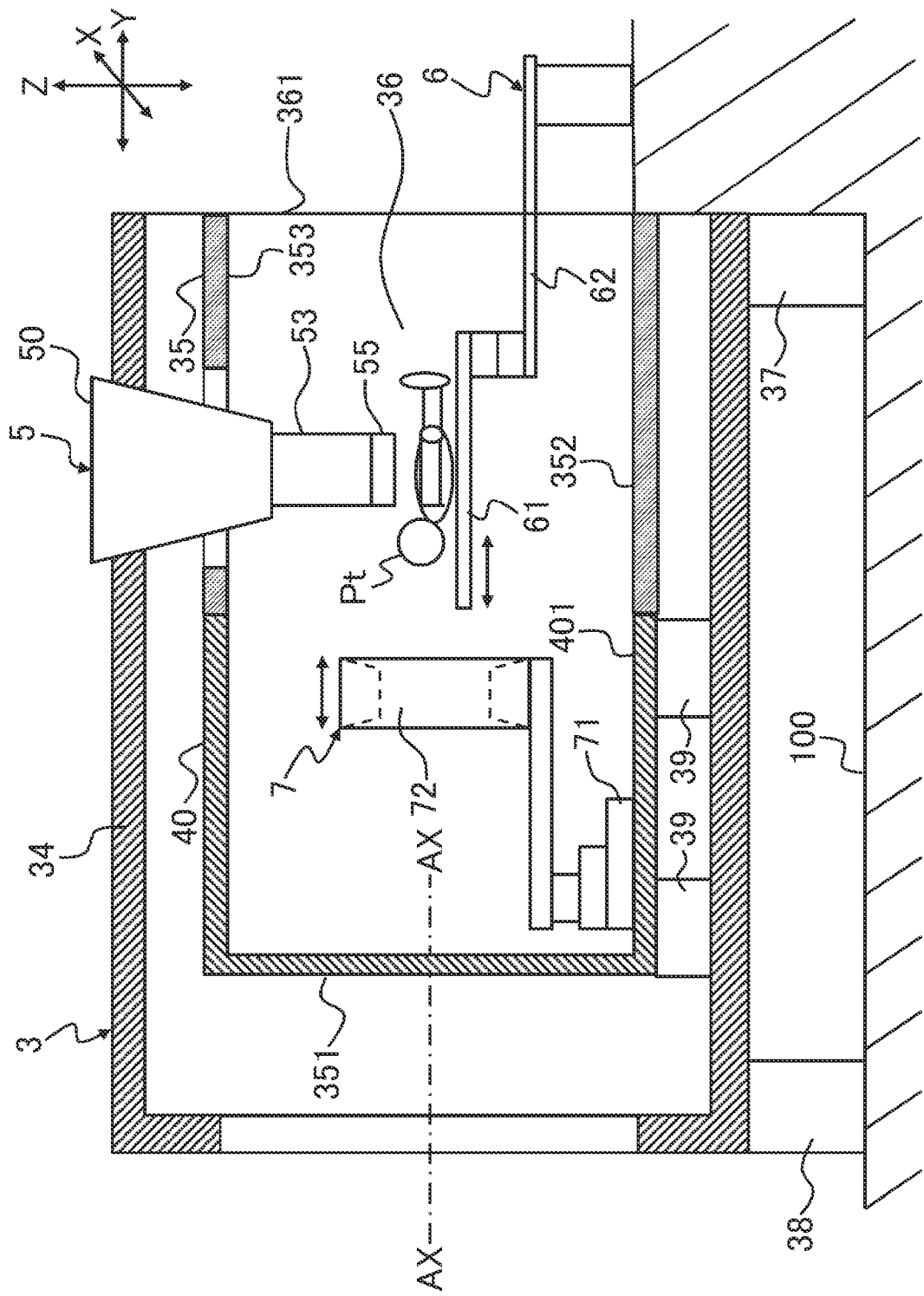
FIG. 3 is a schematic block diagram of a rotary gantry.

A description will be given to an overview of the mechanical configuration of the rotary gantry 3 with reference to FIG. 3. The rotary gantry 3 includes: a cylindrical rotary barrel 34; an annular radiation therapy cage 35 positioned inside the rotary barrel 34 and provided coaxially with the rotary barrel 34; and a cylindrical stationary ring 40 positioned inside the rotary barrel 34 and provided coaxially with the rotary barrel 34. The irradiation apparatus 53 is secured relative to the rotary barrel 34 and the radiation therapy cage 35 and revolves around an isocenter IC in conjunction with rotation of the rotary barrel 34 and the radiation therapy cage 35. The following description will be given to an example in which the rotary barrel 34, the radiation therapy cage 35, and the stationary ring 40 are cylindrically or annularly formed. Instead, the rotary barrel 34 and the like may be formed in a rectangular shape or in a truss structure.

The rotary barrel 34 is provided with a ring-shaped front ring in front of the rotary barrel and is also provided with a ring-shaped rear ring behind the rotary barrel (neither of these rings is shown). The front ring is supported from beneath by a supporting apparatus 37 installed on the floor 100 of the building. The rear ring is supported from beneath by a supporting apparatus 38 installed on the floor 100.

The supporting apparatus 37 includes a pair of roll support members and a plurality of support rollers (neither of these items is shown). Each support roller is rotatably attached to each roll support member. The front ring is rotatably supported by each support roller.

Like the supporting apparatus 37, the supporting apparatus 38 also includes a pair of roll support members and a plurality of support rollers (neither of these items is shown). Each support roller is rotatably attached to each roll support member. The rear ring is rotatably supported by each support roller.

The rotation axis of a rotating apparatus rotating the rotary gantry 3 is coupled with the rotation axis of one support roller of the support rollers supporting the rear ring via a decelerating apparatus (neither the rotating apparatus nor the decelerating apparatus is shown). An angle detector (not shown) measuring a rotation angle of the rotary gantry 3 is coupled with the rotation axis of one support roller of the support rollers supporting the front ring.

A description will be given to the radiation therapy cage 35. In the following description, the radiation therapy cage may be shortened to a therapy cage 35. The therapy cage 35 is provided at an opening of the rotary barrel 34 on the front ring side. The interior of the therapy cage 35 is formed in such a shape that an alphabetic character "D" is titled through 90 degrees by a moving floor 352 parallel to the floor 100 of the building 10 and an arc-shaped arc portion 353. Inside the therapy cage 35, a plate material coupled like a crawler is disposed and the plate material rotates together with the rotary barrel 34 and the therapy cage 35 and forms the level moving floor 352. Both ends of the therapy cage 35 are open and the front ring-side end provides an entrance 361 for the top plate 61 to enter or exit from the irradiation chamber 36.

At an end of both ends of the therapy cage 35 positioned opposite to the entrance 361, the stationary ring 40 is disposed. Inside the stationary ring 40, a horizontal floor portion 401 is formed. An end of both ends of the stationary ring 40 positioned opposite to the therapy cage 35 is sealed with a panel 351. The stationary ring 40 is rotated in an opposite direction to the rotary barrel 34 by a drive mechanism 39 provided in the rotary barrel 34. As a result, the horizontal floor portion 401 is not rotated relative to the building 10 even when the rotary barrel 34 is rotated. The CT apparatus 7 is movably provided on the horizontal floor portion 401 as described later.

The thus configured therapy cage 35 ensures the safety of a patient Pt on the top plate 61 on a movement path (revolving path) of the irradiation apparatus 5 in the circumferential direction of the rotary gantry 3. Further, the therapy cage 35 provides the moving floor 352 as scaffolding so that a medical technologist can exercise a medical practice on a patient Pt. The therapy cage 35 provides the surroundings with a closed space as the irradiation chamber 36. The stationary ring 40 provides the building 10 with the stationary horizontal floor portion 401. The therapy cage 35 provides the surroundings with a closed space to be a retraction place for the CT apparatus 7.

The CT apparatus 7 is provided so as to be positioned in the stationary ring 40. The CT apparatus 7 picks up an image of an affected part by a patient Pt being passed through an opening 72. The CT apparatus 7 is moved in the therapy cage 35 by the moving mechanism 71. The CT apparatus 7 is capable of being moved in parallel to the moving floor 352 and is also capable of being moved at an angle different from that of the moving floor 352. That is, the moving mechanism 71 may be so configured as to move the CT apparatus 7 using a rail or may be so configured that the CT apparatus 7 can be tilted from the X axis. Or, the moving mechanism may be configured as a multi-axial robot arm. Adoption of a configuration in which the CT apparatus 7 can be tilted from the X axis allows the CT apparatus 7 to be moved in accordance with the orientation of the top plate 61. The moving mechanism 71 moves the top plate 61 above the moving floor 352 of the rotary gantry 3 so as to prevent contact with the moving floor 352.

Figure 4:
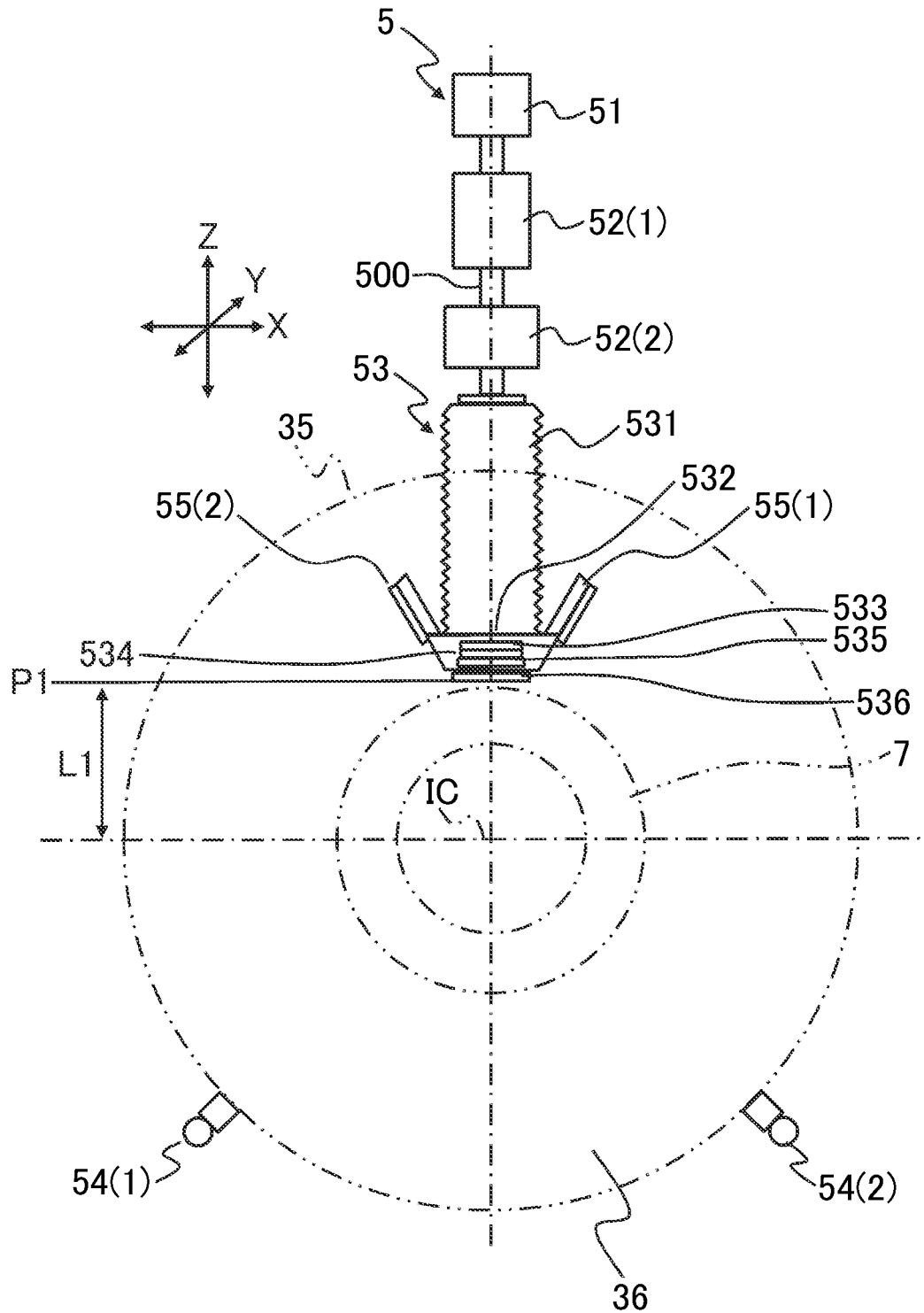
FIG. 4 is an explanatory drawing illustrating a position of an irradiation nozzle at a time of CT imaging.

FIG. 4 is a block diagram of the irradiation apparatus 5 as viewed from a front direction of the rotary gantry 3. FIG. 4 indicates a position of the irradiation nozzle 53 during imaging with the CT apparatus 7.

On the beam path 500 of the irradiation apparatus 5, the Y-direction scanning electromagnet 51, the first X-direction scanning electromagnet 52(1), the second X-direction scanning electromagnet 52(2), and the irradiation nozzle 53 are provided in this order from above. The irradiation nozzle 53 includes: the bellows pipe 531, the window 532 provided on the tip side of the bellows pipe 531; the main dose monitor 533 provided below the window 532; and sub-dose monitor 534 provided below the main dose monitor 533; the position monitor 535 provided below the dose monitor 534; and the ridge filter 536 provided below the position monitor 535. Further, the irradiation nozzle 53 is provided at the tip of the irradiation nozzle with X-ray detectors (FPDs: Flat Panel Detectors) 55(1), 55(2).

The dose monitors 533, 534 measure a dose of a particle ray and transmits the measured dose to the irradiation control system 82. The position monitor 535 measures an emission position of a particle ray and transmits the measured emission position to the irradiation control system 82.

The FPDs 55(1), 55(2) correspond to X-ray irradiation apparatuses 54(1), 54(2) disposed at the lower part of the irradiation chamber 36. That is, the first FPD 55(1) detects an X ray applied from the first X-ray irradiation apparatus 54(1) and transmits a result of the detection to the irradiation control system 82. The second FPD 55(2) detects an X-ray applied from the second X-ray irradiation apparatus 54(2) and transmits a result of the detection to the irradiation control system 82. Owing to the X-ray irradiation apparatuses 54(1), 54(2) and the FPDs 55(1), 55(2), a position of an affected part under radiation therapy can be tracked. When not specially distinguished, the X-ray irradiation apparatuses 54(1), 54(2) will be designated as X-ray irradiation apparatuses 54 and the FPDs 55(1), 55(2) will be designated as FPDs 55. During imaging, the FPDs 55 are folded to the irradiation nozzle 53 side to prevent contact with the CT apparatus 7. Instead, the irradiation nozzle 53 may be retracted to a position where the FPDs 55 are not brought into contact with the CT apparatus 7 without folding the FPDs 55.

The bellows pipe 531 is extended and retracted in a Z direction in FIG. 4. An amount of extension/retraction of the bellows pipe 531 is detected with a sensor, not shown, and is transmitted to the irradiation control system 82. As shown in FIG. 4, during imaging with the CT apparatus 7, the bellows pipe 531 is retracted to retract the tip of the irradiation nozzle 53 to the waiting position P1. The tip (undersurface of the ridge filter 536) of the irradiation nozzle 53 and an isocenter IC is spaced from each other by a distance of L1. As a result, even when the CT apparatus 7 is moved toward the area below the irradiation apparatus 5 in the irradiation chamber 36, the irradiation apparatus 5 and the CT apparatus 7 do not interfere with each other. When the CT apparatus 7 is large-sized and the spacing between the tip of the irradiation nozzle 53 and an isocenter IC is increased, the scanning electromagnets 51, 52 and the electromagnets 32 located at the upper part of the irradiation nozzle 53 may also be moved up or down.

Figure 5:
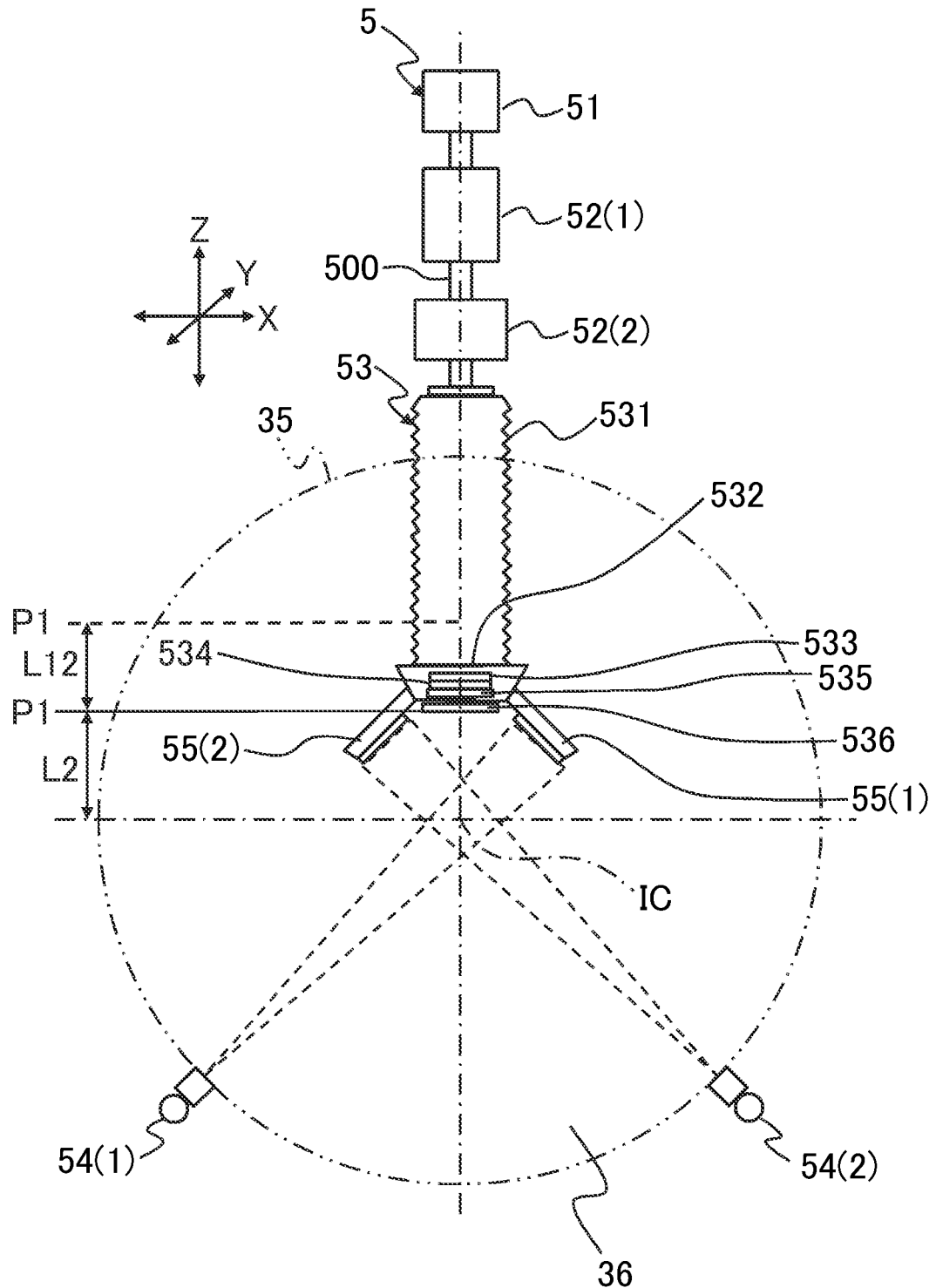
FIG. 5 is an explanatory drawing illustrating a position of an irradiation nozzle taken when applying a particle ray while tracking a moving body.

FIG. 5 illustrates a position of the irradiation nozzle 53 in moving body tracking irradiation. In this irradiation, a particle ray is applied from the irradiation apparatus 5 toward an affected part of a patient Pt while tracking the movement of issues of the patient Pt with the X-ray irradiation apparatuses 54 and the FPDs 55 in real time. In case of moving body tracking irradiation, the FPDs 55 are moved down to a position opposite the X-ray irradiation apparatuses 54 so that an X ray applied from the X-ray irradiation apparatuses 54 can be detected.

As the result of the bellows pipe 531 being extended downward by a length of L12 from a state shown in FIG. 4, the tip of the irradiation nozzle 53 arrives at a moving body tracking irradiation position P2. At this time, a distance from the tip of the irradiation nozzle 53 to the isocenter IC is as indicated by L2 (<L1). The distance of L2 is set to such a value that the irradiation nozzle is in proximity to the patient Pt but the irradiation nozzle 53 or the FPDs 55 are not in contact with the patient Pt.

Figure 6:
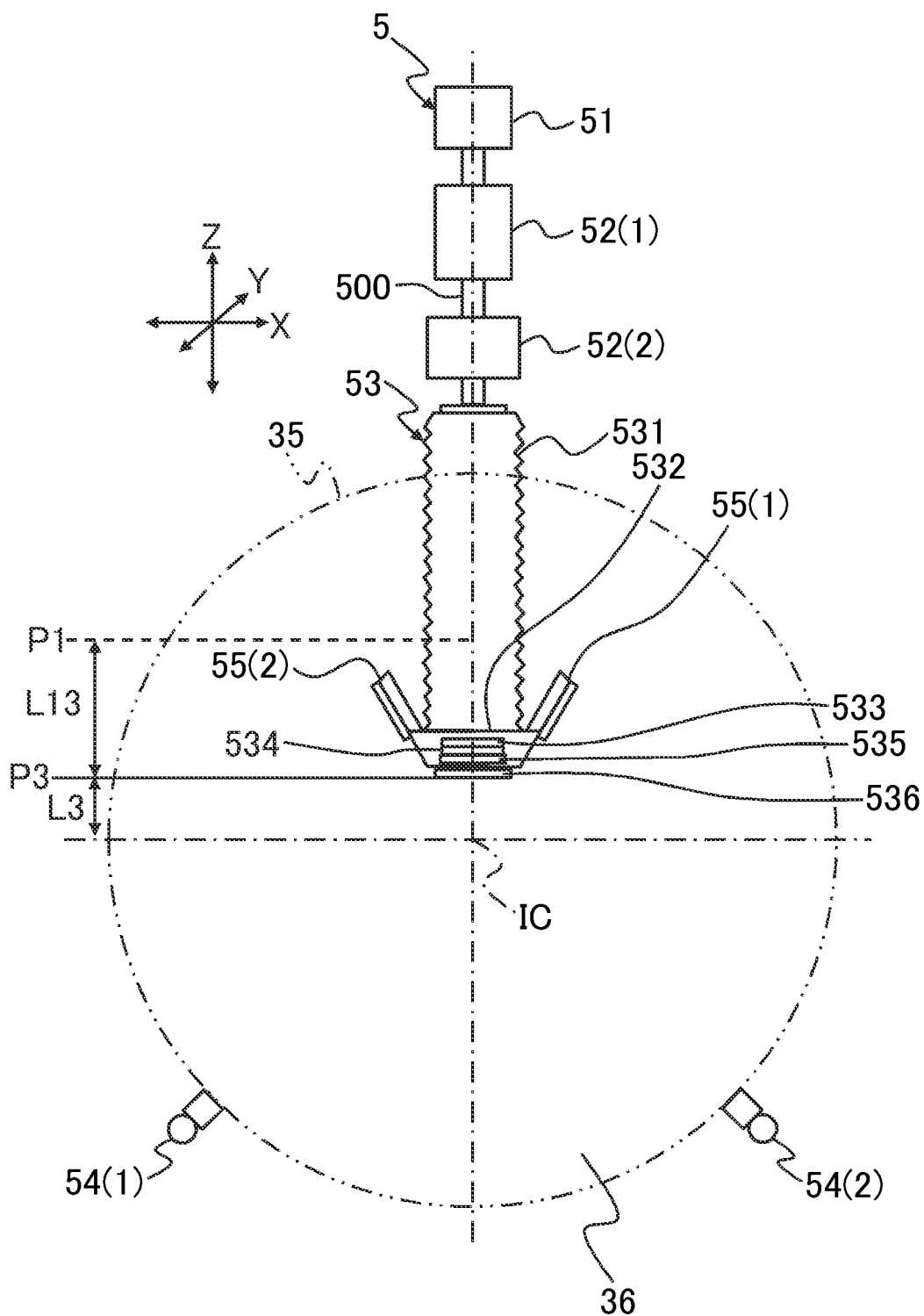
FIG. 6 is an explanatory drawing a position of an irradiation nozzle taken when most closely approaching an affected part and applying a highly precise particle ray.

FIG. 6 illustrates a position of the irradiation nozzle 53 taken when the irradiation nozzle is brought closest to an affected part and a highly precise particle ray is applied.

As the result of the bellows pipe 531 being extended downward by a length of L13 from, for example, a state shown in FIG. 4, the tip of the irradiation nozzle 53 arrives at a closest irradiation position P3. At this time, a distance from the tip of the irradiation nozzle 53 to the isocenter IC is as indicated by L3 (<L2).

In the closest irradiation position P3 in this embodiment, the FPDs 55 are folded to the irradiation nozzle 53 side; therefore, moving body tracking by an X ray is not performed. By an amount equivalent to an amount by which the FPDs 55 are folded, the irradiation nozzle 53 can be brought close to a patient Pt. When the FPDs 55 can receive an X ray from the X-ray irradiation apparatuses 54 by changing a mounting position of the FPDs 55 or taking any other like measures, moving body tracking may be performed.

In the above description, a case where the tip of the irradiation nozzle 53 is moved from the waiting position P1 to the moving body tracking irradiation position P2 or the closest irradiation position P3 is taken as an example. However, the tip of the irradiation nozzle 53 can be moved between the positions P1, P2, P3. That is, the tip of the irradiation nozzle is movable from the position P1 to the position P2, from the position P1 to the position P3, from the position P2 to the position P1, from the position P2 to the position P3, from the position P3 to the position P1, and from the position P3 to the position P2.

Figure 7:
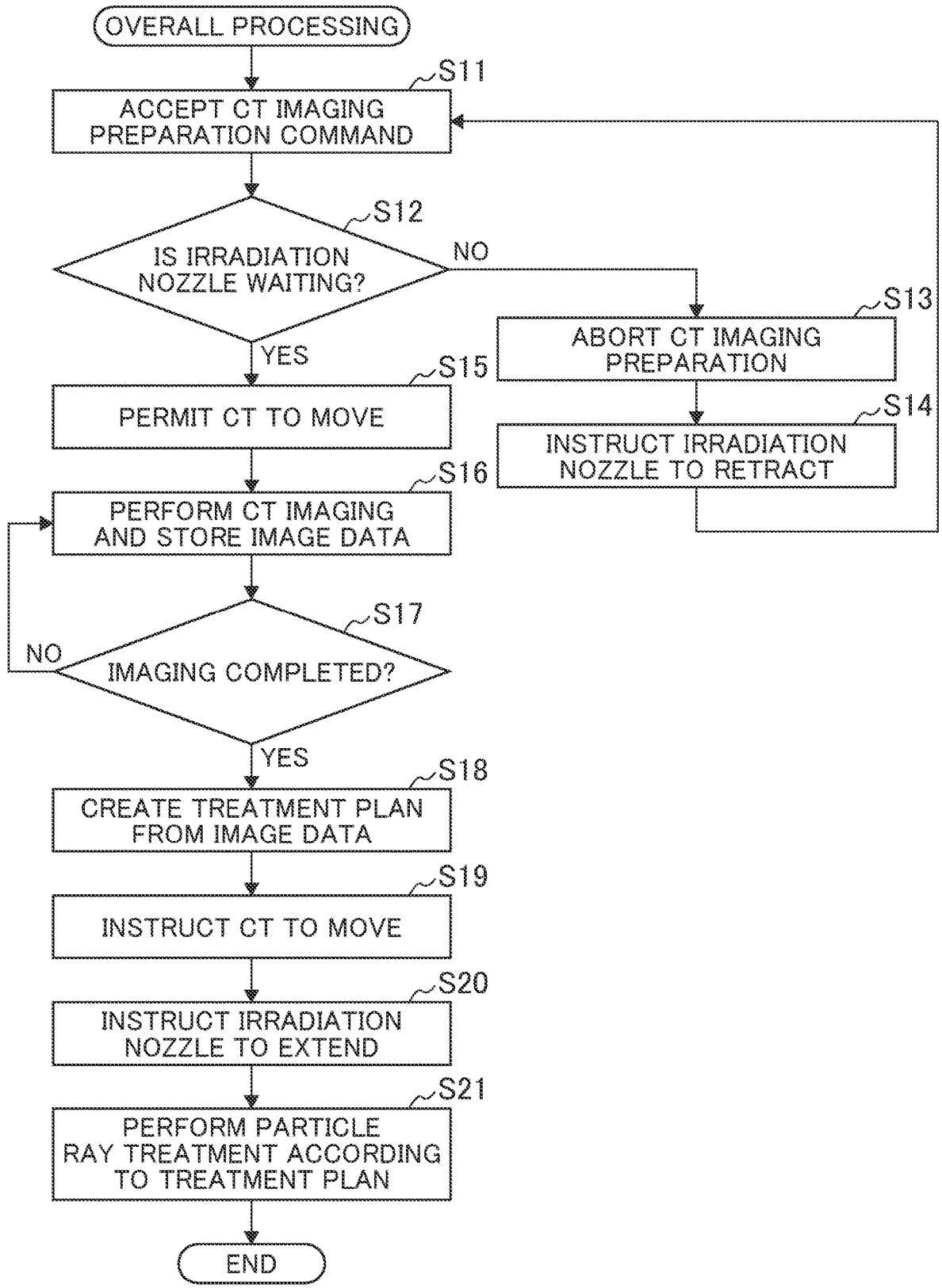
FIG. 7 is a flowchart illustrating overall processing by a particle ray therapy apparatus.

A description will be given to a control method of the particle ray therapy apparatus 1 with reference to FIG. 7.

When the main controller 81 is instructed to start preparation for imaging with the CT apparatus 7 from the operation terminal 86 (S11), the main controller checks a position of the irradiation nozzle 53 via the irradiation control system 82. Then, the main controller determines whether the irradiation nozzle 53 has been retracted to the waiting position P1 (S12).

When the main controller 81 determines that the irradiation nozzle 53 has not been retracted (S12: NO), the main controller aborts the preparation for imaging with the CT apparatus 7 (S13), and instructs the irradiation apparatus 5 to retract the irradiation nozzle 53 and retract itself. This instruction is sent, for example, from the main controller 81 to the irradiation apparatus 5 by way of the irradiation control system 82. As a result, the irradiation apparatus 5 retracts the tip of the irradiation nozzle 53 to the predetermined waiting position P1.

When a user instructs a start of preparation for imaging with the CT apparatus 7 from the operation terminal 86 again (S11), the main controller 81 determines that the tip of the irradiation nozzle 53 has been retracted (S12: YES) and permits the CT apparatus 7 to move into the irradiation chamber 36 (S15). That is, the main controller 81 permits the CT control system 84 the movement of and imaging with the CT apparatus 7. Since the irradiation nozzle 53 has been retracted, the CT apparatus 7 and the irradiation nozzle 53 are not brought into contact with each other even when the CT apparatus 7 moves from the standby location into the irradiation chamber 36.

The CT apparatus 7 permitted to move moves from the standby location at the back of the therapy cage 35 toward the irradiation chamber 36, picks up an image of a patient Pt on the top plate 61, and transmits obtained image data to the data accumulation unit 85 and causes the image data to be stored there (S16). Specifically, the CT apparatus 7 moves from the predetermined standby location to a treatment position in the irradiation chamber 36 according to an instruction from the CT control system 84. (The treatment position corresponds to an isocenter IC and is a place where an image of an affected part of a patient Pt can be picked up.) The CT apparatus 7 passes a patient Pt through the opening 72 of the CT apparatus 7 from the leading end of the top plate 61 in accordance with an angle of the top plate 61 and moves to a place where an image of an affected part can be picked up and stops there. Thereafter, the CT apparatus 7 picks up an image of the vicinity of the isocenter IC and transmits obtained image data to the CT control system 84. The CT control system 84 stores the image data received from the CT apparatus 7 in the data accumulation unit 85.

The main controller 81 confirms whether imaging with the CT apparatus 7 has been completed via the CT control system 84 (S17). After the main controller 81 confirms completion of imaging with the CT apparatus 7 (S17: YES), the treatment plan apparatus 83 creates a treatment plan based on the image data stored in the data accumulation unit 85 (S18). Creating of a treatment plan is performed in accordance with a manual instruction from a doctor. The created treatment plan is transferred to the data accumulation unit 85 and stored there. Instead of creation of a treatment plan, a treatment plan created beforehand may be modified based on image data.

The main controller 81 instructs the CT apparatus 7 to return to the standby location in accordance with a treatment start instruction inputted from the operation terminal 86 (S19). Simultaneously with a movement instruction to the CT apparatus 7 or after a movement instruction to the CT apparatus 7, the main controller 81 instructs the irradiation nozzle 53 to extend to the irradiation position P2 or P3 (S20). Thus, smooth transition from CT imaging to beam irradiation treatment can be implemented without moving a patient Pt.

When the irradiation nozzle 53 arrives at the irradiation position P2 or the irradiation position P3, the irradiation control system 82 causes a predetermined particle ray to be applied from the irradiation nozzle 53 to the isocenter IC in accordance with a treatment plan (S21).

Figure 8:
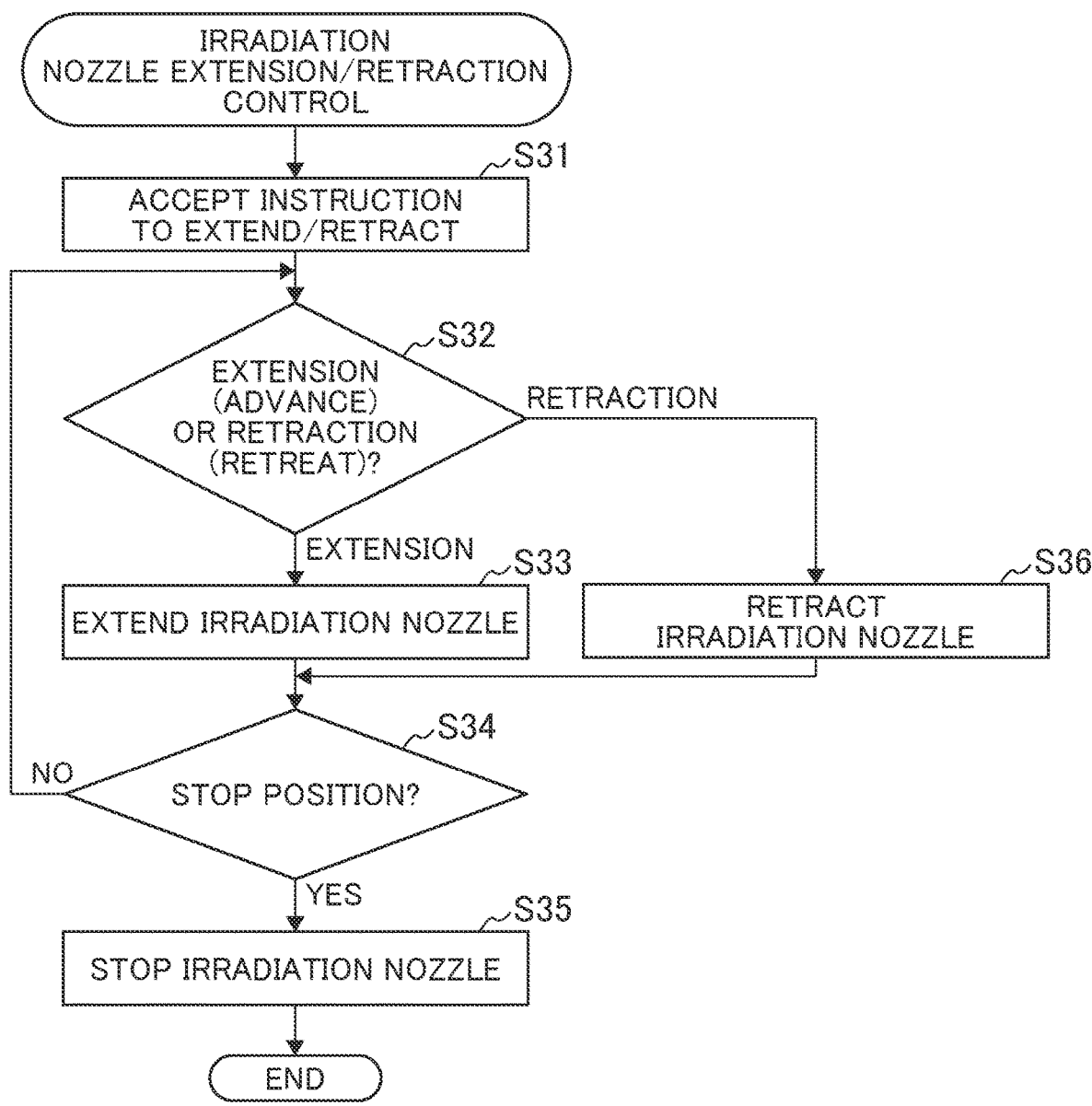
FIG. 8 is a flowchart illustrating processing of controlling a position of an irradiation nozzle.

FIG. 8 is a flowchart illustrating processing of controlling extension/retraction of the irradiation nozzle. When the irradiation control system 82 accepts an instruction to extend or retract the irradiation nozzle 53 from the main controller 81 (S31), the irradiation control system determines whether the instruction is to extend or retract (S32). "Extend" cited here refers to moving the tip of the irradiation nozzle 53 toward an isocenter IC. "Retract" refers to moving and bringing the tip of the irradiation nozzle 53 away from an isocenter IC.

When instructed to extend the irradiation nozzle 53 (S32: Extend), the irradiation control system 82 extends the irradiation nozzle 53 (S33). The irradiation control system 82 determines whether the tip of the irradiation nozzle 53 arrives at a stop position (S34) and extends the tip of the irradiation nozzle 53 until the tip arrives at the stop position (S34: NO→S32: Extend→S33). When the irradiation control system 82 determines that the tip of the irradiation nozzle 53 has arrived at the stop position (S34: YES), the irradiation control system stops the irradiation nozzle 53 extending.

Meanwhile, when instructed to retract the irradiation nozzle 53 (S32: Retract), the irradiation control system 82 retracts the irradiation nozzle 53 (S36). The irradiation control system 82 determines whether the tip of the irradiation nozzle 53 arrives at a stop position (S34) and retracts the irradiation nozzle 53 until the tip arrives at the stop position (S34: NO→S32: Retract→S36). When the irradiation control system 82 determines that the tip of the irradiation nozzle 53 has arrived at the stop position (S34: YES), the irradiation control system stops the irradiation nozzle 53 retracting (S35).

Figure 9:
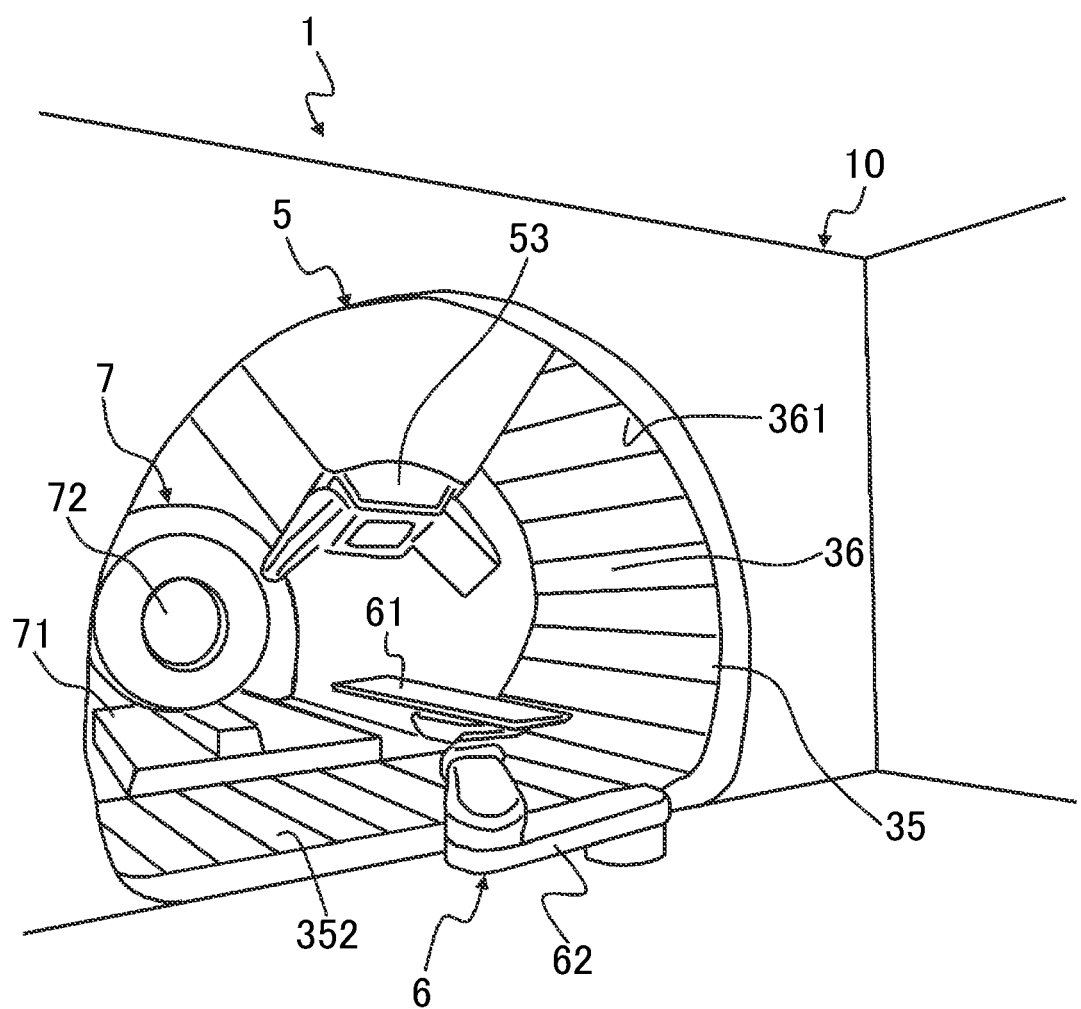
FIG. 9 is a perspective view illustrating an example of a particle ray therapy apparatus.

FIG. 9 is a perspective view partially illustrating an example of an application of the particle ray therapy apparatus 1. The particle ray therapy apparatus 1 is installed in the building 10. The treatment bed 6 is positioned in a space located on the foreground side of the drawing and causes the top plate 61 to enter or exit from the irradiation chamber 36 through the entrance 361.

At the back of the irradiation chamber 36, the CT apparatus 7 is so provided that the CT apparatus is movable toward the irradiation chamber 36 (to an area that can be irradiated with the irradiation apparatus 5). In FIG. 9, the CT apparatus 7 is positioned in the standby location and is moved to the foreground direction for imaging.

According to the thus configured present embodiment, the treatment bed 6 and the CT apparatus 7 capable of respectively moving from different directions toward the irradiation chamber 36 formed inside the rotary gantry. Further, the irradiation nozzle 53 retracts to avoid interference with the CT apparatus 7 at a time of imaging and extends and approaches an isocenter IC at a time of treatment.

Therefore, the particle ray therapy apparatus 1 according to the present embodiment is capable of being smoothly switched between imaging with the CT apparatus 7 and treatment with the irradiation apparatus 5 without displacing a patient Pt positioned at an isocenter IC. As a result, a highly reliable treatment plan can be created from image data of an affected part in a state closer to a state of the affected part under treatment; further, during treatment, the irradiation nozzle 53 can be brought closer to the affected part to apply a particle ray. Therefore, the reliability of particle ray treatment can be enhanced.

With the particle ray therapy apparatus 1 according to the present embodiment, a patient Pt need not be moved during a period from imaging with CT apparatus 7 to particle ray irradiation treatment. Consequently, displacement of an affected part can be suppressed between when a treatment plan is created and when a treatment is performed. Therefore, a margin in setting a range of application to an affected part can be reduced and thus an influence on normal tissues can be reduced.

In the particle ray therapy apparatus 1 according to the present embodiment, the CT apparatus 7 can be housed at the back of the irradiation chamber 36 and a CT image can be acquired at an isocenter IC in the irradiation chamber 36 and thus, a high-quality treatment plan can be created. Further, since a simulation chamber need not be separately provided for creating treatment plans, a building can be downsized.

The particle ray therapy apparatus 1 according to the present embodiment can be relatively smoothly switched between CT imaging and treatment and thus, a treatment plan can be optimized in a shorter time than conventional and real-time adaptive therapy (adaptive radiation therapy) can be implement.

In the particle ray therapy apparatus 1 according to the present embodiment, the top plate 61 of the treatment bed 6 and the CT apparatus 7 are mechanically separated from each other. The top plate 61 can freely enter or exit from the irradiation chamber 36 and an angle (posture) of the top plate can be altered without being restricted by a structure of the CT apparatus 7. Therefore, the degree of freedom in treatment is increased and the ease of use of treatment is enhanced.

Second Embodiment

A description will be given to Second Embodiment with reference to FIG. 10. The descriptions of the following embodiments, including the present embodiment, will be focused on a difference from First Embodiment.

Figure 10:
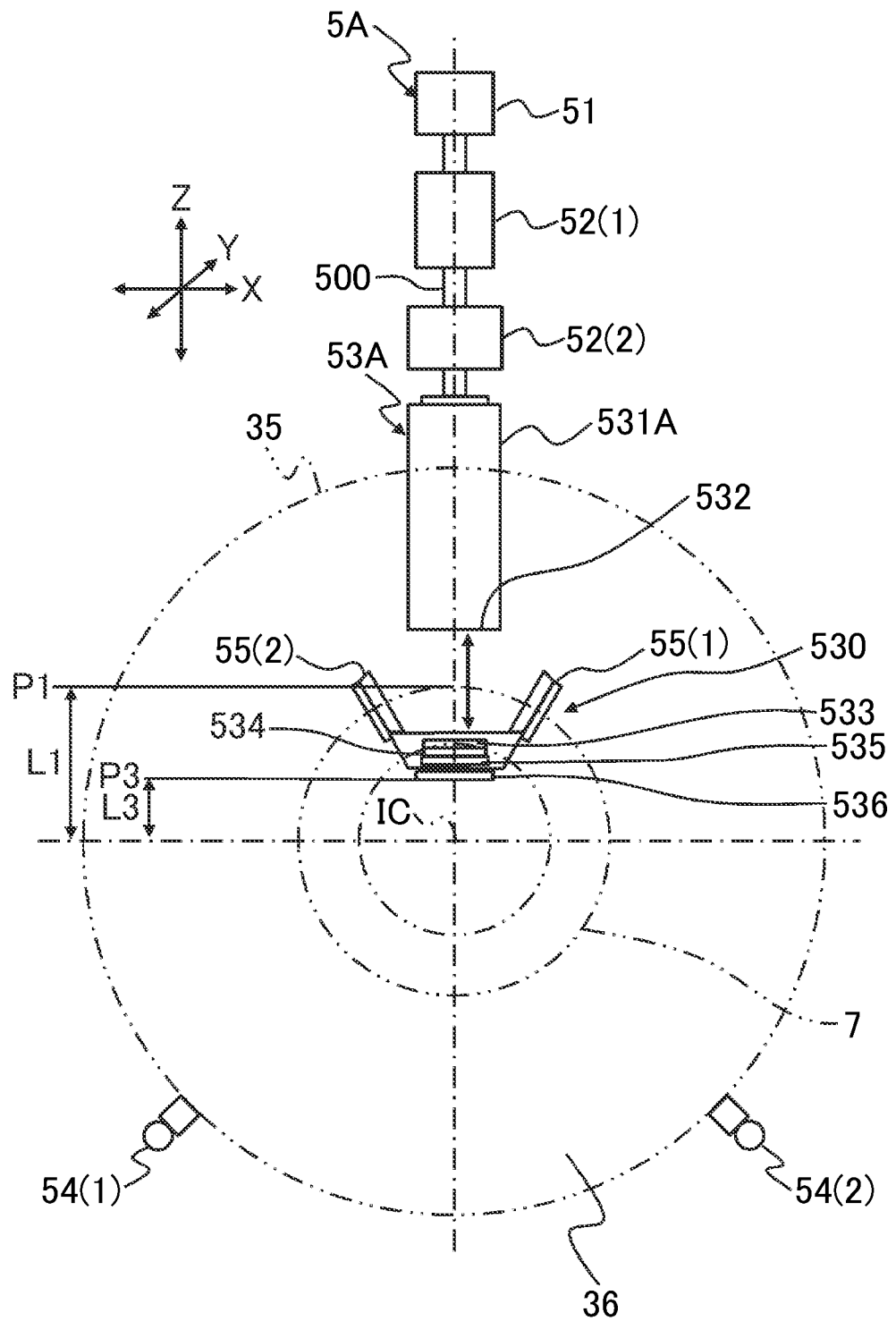
FIG. 10 is an explanatory drawing illustrating a position of an irradiation nozzle taken when most closely approaching in accordance with Second Embodiment.

FIG. 10 is an explanatory drawing illustrating an irradiation nozzle 53A of an irradiation apparatus 5A according to the present embodiment. The present embodiment adopts a single pipe 531A in place of the bellows pipe 531. In the present embodiment, a tip portion 530 comprised of monitors 533 to 536 is separated from the single pipe 531A so that the tip portion is movable. The tip portion 530 may also be referred to as a separated monitor portion 530.

FIG. 10 illustrates a case where the irradiation nozzle 53A is located in the closest irradiation position P3. The separated tip portion 530 can be moved to the waiting position P1, moving body tracking irradiation position P2, and closest irradiation position P3 described in relation to First Embodiment by a tip portion moving mechanism, not shown.

The present embodiment also brings about the same working-effects as First Embodiment does. In the irradiation apparatus 5A according to the present invention, the single pipe 531A is used and the tip portion 530 separated from the single pipe 531A is moved; therefore, a particle ray emitted from the window 532 of the single pipe 531A slightly spreads in the air. A particle ray emitted into the air passes through the tip portion and, as a result, further spreads. However, since the tip portion 530 approaches an affected part as in First Embodiment during application of a particle ray, the spread of a beam at an affected part can be suppressed.

In the present embodiment, the single pipe 531A that does not extend is used in place of the extensible bellows pipe 531 and the tip portion 530 is separated and moved. Therefore, overall dimensions of the irradiation apparatus 5A can be reduced and a manufacturing cost of the irradiation apparatus 5A can be reduced. Specifically, an overall length of the bellows pipe 531 is several times a required amount of extension (stroke amount) and a cost of the bellows pipe is higher than that of the single pipe. On the other hand, since the present embodiment adopts the single pipe 531A, a size of the irradiation apparatus 5A and a size of the rotary gantry can be reduced and thus, a cost can also be reduced. As compared with the bellows pipe 531, the single pipe 531A is simpler in configuration and reduction of a failure probability and simplification of maintenance work can be implemented.

Third Embodiment

A description will be given to Third Embodiment with reference to FIG. 11. The description will be given to a direction in which the irradiation apparatus 5 is extensible (can be advanced and retreated) in relation to the present embodiment.

Figure 11:
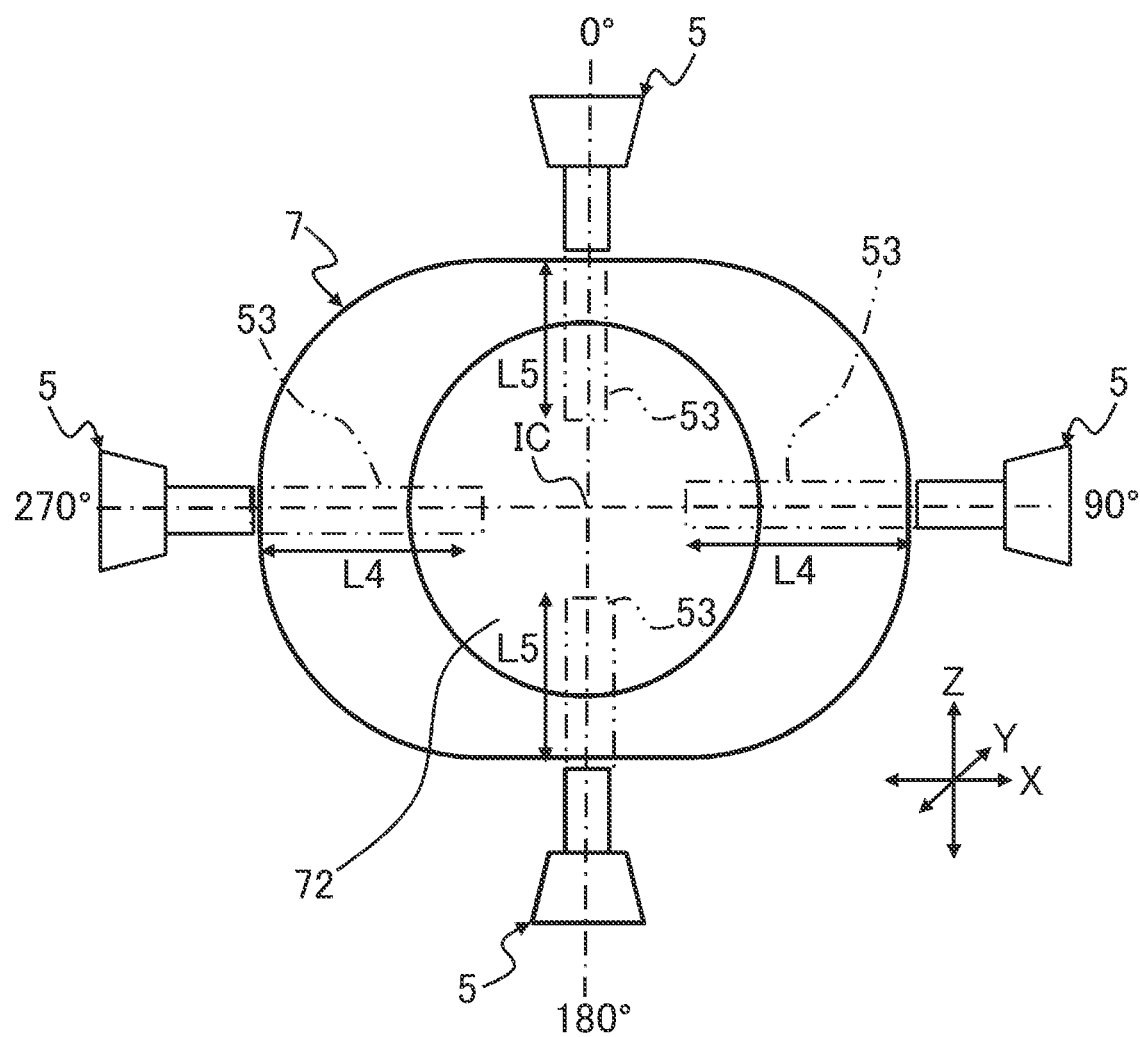
FIG. 11 is a schematic drawing illustrating a positional relation between a CT apparatus and an irradiation nozzle as viewed from front in accordance with Third Embodiment.

FIG. 11 is an explanatory drawing schematically illustrating a positional relation between the CT apparatus 7 and the irradiation apparatus 5. A contour of the CT apparatus 7 is not always circular and may be non-circular, such as rectangular or oval.

Though not shown in the drawing, in cases where a contour of the CT apparatus 7 is substantially a perfect circle, a length by which the irradiation nozzle 53 should extend or retract (also referred to as extension/retraction amount or stroke amount) for prevention of interference does not vary so much wherever the irradiation apparatus 5 is positioned on the circumferential side of the CT apparatus 7. That is, when a point immediately above the center of the CT apparatus 7 is assumed to be at 0°, an extension/retraction amount required for the irradiation nozzle 53 to avoid interference with the CT apparatus 7 is substantially identical at almost all the angles of 0°, 90°, 180°, 270°, and any other angle between these four angles.

Meanwhile, when a contour of the CT apparatus 7 is in a non-circle, for example, in a horizontally long oval or rectangle as shown in FIG. 11, an amount by which the irradiation nozzle 53 should extend or retract varies depending to a revolving angle of the irradiation apparatus 5. A distance, L4, from an isocenter IC to the circumference of the CT apparatus 7 taken when the irradiation apparatus 5 is positioned at 90° or 270° is longer than a distance, L5, from the isocenter IC to the circumference of the CT apparatus 7 taken when the irradiation apparatus 5 is positioned at 0° or 180°.

In this example, four angles of 0°, 90°, 180°, and 270° are taken as an example; however, the irradiation nozzle 53 may be configured to be extensible at any other angle than these angles, for example, at any angle within ranges of 1° to 89°, 91° to 179°, 181° to 269°, and 271° to 359°.

When a length from an isocenter IC to the circumference of the CT apparatus 7 differs depending on an angle of the irradiation apparatus 5, as mentioned above, a minimum extension/retraction amount required for preventing contact between the irradiation nozzle 53 and the CT apparatus 7 also differs.

The irradiation nozzle 53 can be configured to be extensible from a plurality of angles. In this case, since the irradiation nozzle 53 need not be moved to an extensible angle, a time required for switching between particle ray treatment and CT imaging can be shortened and a throughput of the particle ray therapy apparatus 1 can be enhanced. At this time, an extension/retraction amount may be constant at an extension/retraction amount (maximum extension/retraction amount) with which contact with the CT apparatus 7 does not occur at any angle. Further, an extension/retraction amount for avoiding interference may be varied depending on an angle of the irradiation apparatus 5. When an extension/retraction amount is varied depending on angle, a mechanical structure and control processing (correction processing and the like) are complicated and the rotary gantry is accordingly increased in size.

A configuration in which the irradiation nozzle 53 is extracted or retracted at an angle at which an extension/retraction amount is minimized (0° and 180° in the case of FIG. 11) may be adopted. In this case, upsizing of the rotary gantry and complication of control processing can be suppressed.

When the irradiation apparatus 5 is configured to be extensible from an angle of 180°, a gap for extending or retracting the irradiation nozzle 53 is produced in the moving floor 352; therefore, movement of a medical technologist in the irradiation chamber 36 is restricted. This gap could be closed with a plate or the like but in this case, a mechanical structure is complicated.

For this reason, from the viewpoint of not hindering movement of a medical technologist, a configuration in which the irradiation nozzle is extended or restricted at any other angle than an angle at which the irradiation apparatus 5 is positioned on the moving floor 352 (in proximity to 180, for example, within a range of 150° to 210°) may be adopted. In this case, as mentioned above, an extension/retraction amount may be constant at a maximum extension/retraction amount or the irradiation nozzle 53 may be extended or retracted by a minimum required extension/retraction amount for each angle.

An angle at which the irradiation apparatus 5 is extensible may be limited to only 0°. In this case, interference with the CT apparatus 7 can be prevented at a minimum extension/retraction amount. Further, since a gap is not produced in the moving floor 352, a possibility of movement of a medical technologist being hindered is eliminated and ease of use is enhanced. In addition, complication of a mechanical structure and control processing can be suppressed. However, since the irradiation apparatus 5 must be positioned at an angle of 0° before the irradiation nozzle 53 is extended or retracted, a throughput of the particle ray therapy apparatus 1 is degraded.

As mentioned above, it is advisable to take into account complication of a mechanical structure, complication of control processing, upsizing of the rotary gantry, a throughput of therapy, ease of use for medical technologists, a manufacturing cost, and the like when determining from which angle the irradiation nozzle 53 of the irradiation apparatus 5 should be extended or retracted.

The thus configured present embodiment can be combined with either of First Embodiment and Second Embodiment. Further, the present embodiment is also applicable to a configuration in which First Embodiment and Second Embodiment are combined with each other.

Fourth Embodiment

A description will be given to Fourth Embodiment with reference to FIG. 12. In the present embodiment, the treatment bed 6 and the CT apparatus 7 are oppositely disposed to First Embodiment.

Figure 12:
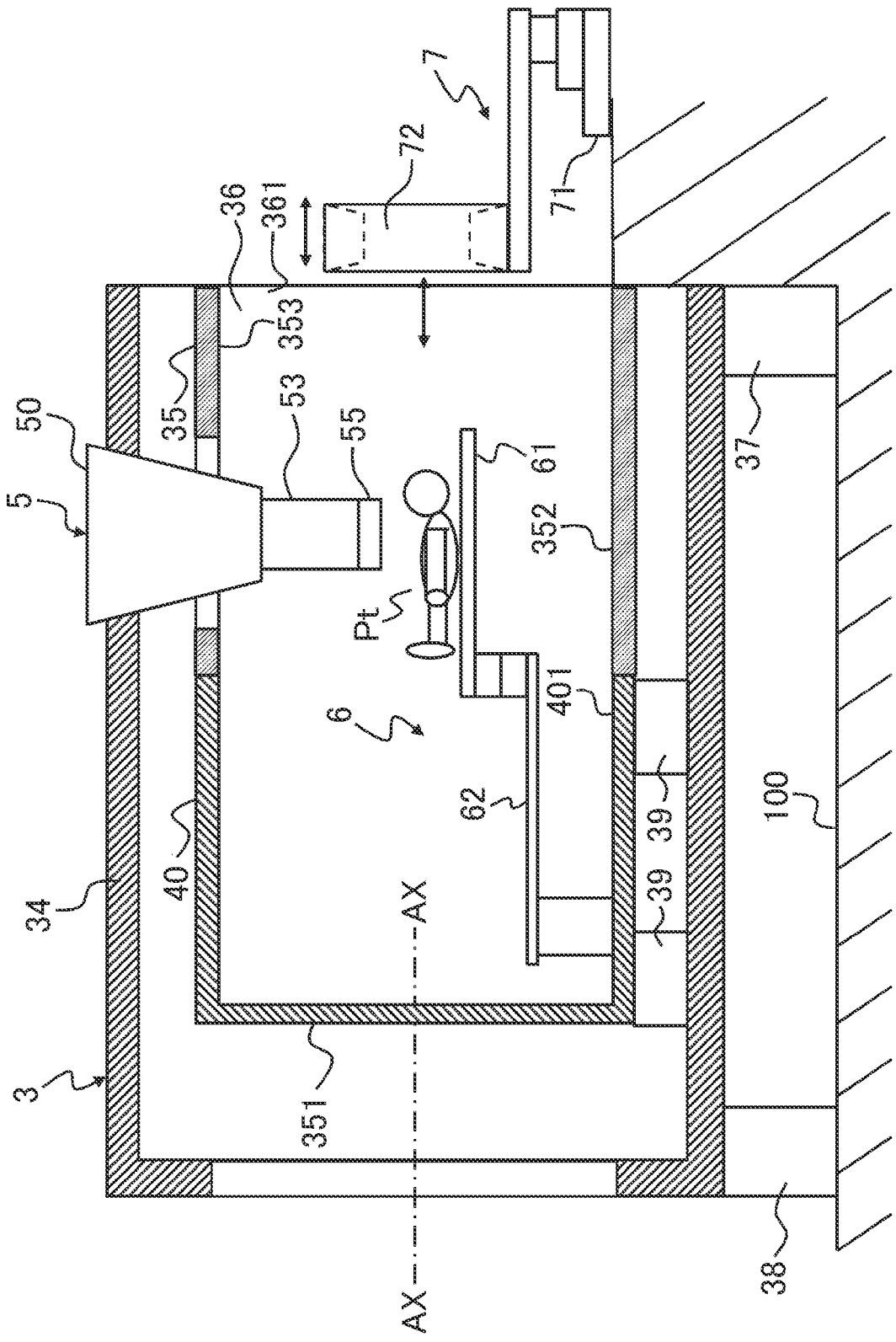
FIG. 12 is an explanatory drawing illustrating a positional relation between a rotary gantry, a CT apparatus, and a treatment bed in according with Fourth Embodiment.

FIG. 12 illustrates a dispositional relation between a rotary gantry 3B, the CT apparatus 7, and the treatment bed 6. The CT apparatus 7 is so disposed as to wait outside the irradiation chamber 36 of the rotary gantry 3B. When permitted to move into the irradiation chamber 36, the CT apparatus 7 is caused to move from outside the irradiation chamber 36 into the irradiation chamber 36 by the moving mechanism 71. This moving mechanism can also be configured not to be brought into contact with the moving floor of the rotary gantry 3B as described in relation to First Embodiment.

The treatment bed 6 is disposed in the therapy cage 35 at the back of the irradiation chamber 36. The thus configured present embodiment also brings about the same working-effects as First Embodiment does. The present embodiment can be combined with any of First to Third Embodiments. Further, the present embodiment is also applicable to any combination of First to Third Embodiments.

Fifth Embodiment

Figure 13:
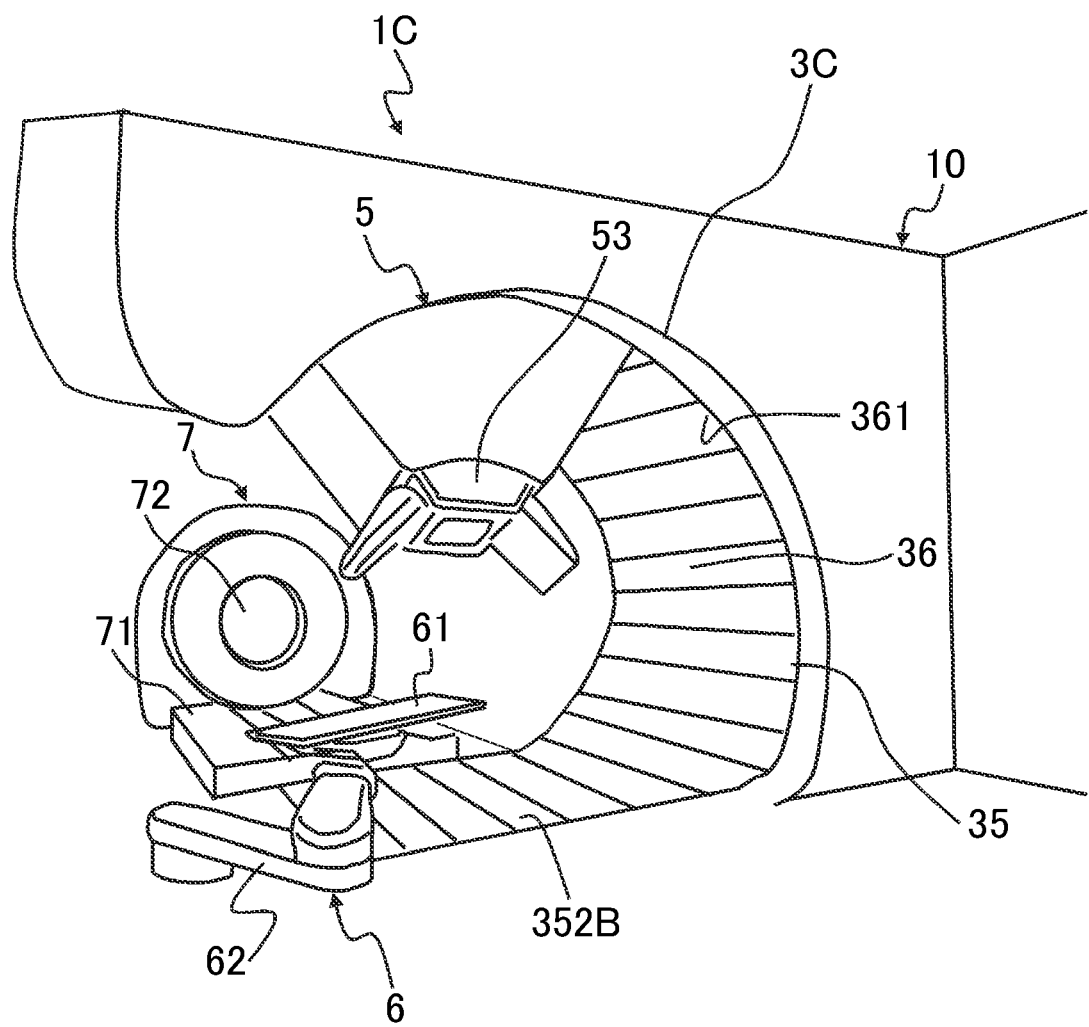
FIG. 13 is a perspective view illustrating an example of a particle ray therapy apparatus in accordance with Fifth Embodiment.
Figure 14:
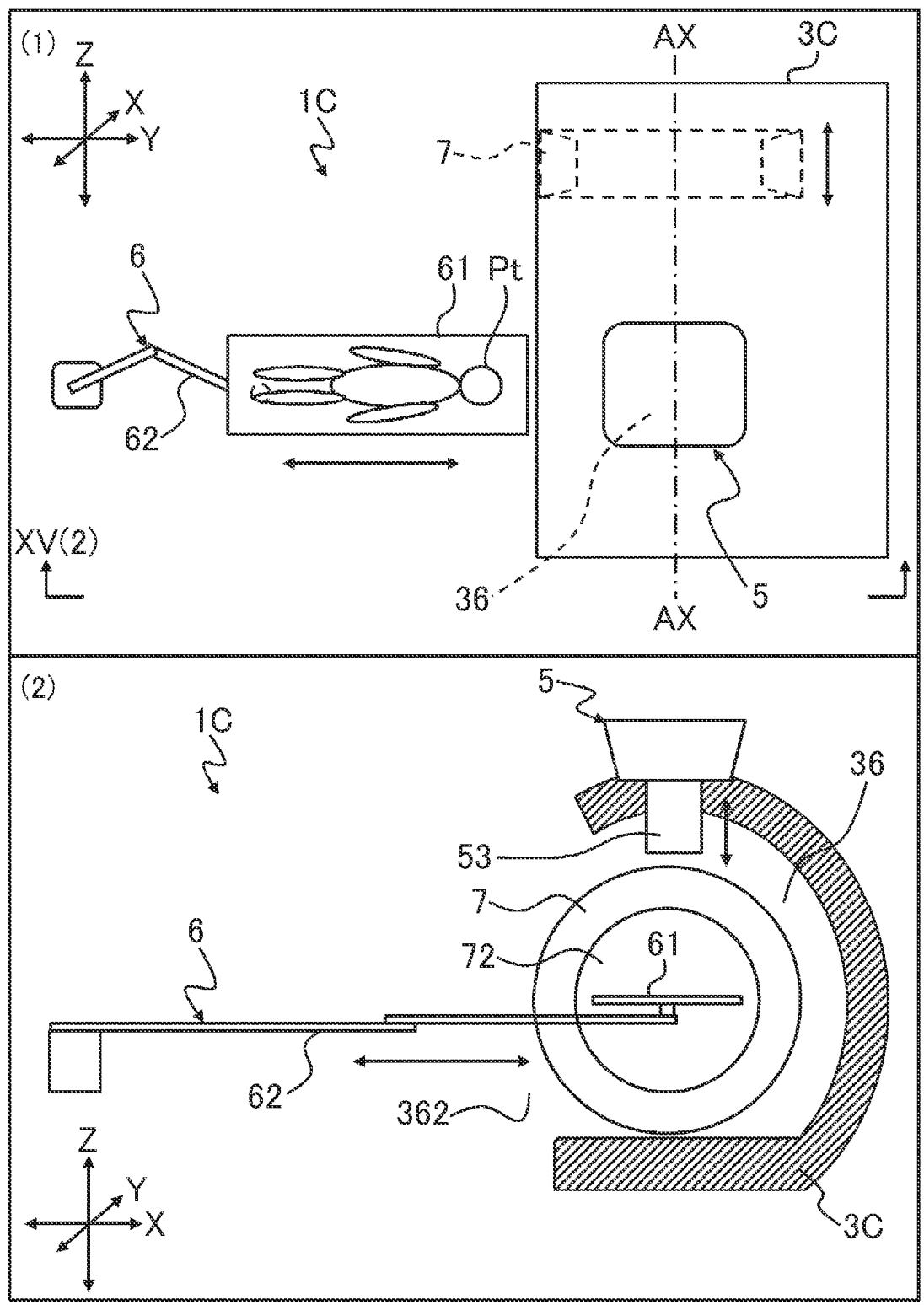
FIG. 14 is an explanatory drawing schematically illustrating a positional relation between a treatment bed, a half gantry, and a CT apparatus.

A description will be given to Fifth Embodiment with reference to FIG. 13 and FIG. 14. In the present embodiment described below, the present invention is applied to a particle ray therapy apparatus 1C using a so-called half-floatating gantry (hereafter, referred to as half gantry) 3C for the rotary gantry. The half gantry 3C circumferentially moves the irradiation apparatus 5 at an angle less than 360° (for example, within a range of −45 degrees to 200 degrees). FIG. 13 is a perspective view partially illustrating an example of the particle ray therapy apparatus 1C equipped with the half gantry 3C. Like the gantry 3 in First Embodiment, the interior of the half gantry 3C is formed in a crawler configuration and constitutes a moving floor 352B parallel to the floor 100. FIG. 14(1) is a plan view of the particle ray therapy apparatus 1C with the top plate 61 positioned outside the irradiation chamber 36. FIG. 14(2) is a side view of the particle ray therapy apparatus 1C as viewed from arrow XV(2) in FIG. 14(1) with the top plate 61 subjected to imaging with the CT apparatus 7 in the irradiation chamber 36. In FIG. 14(2), a patient Pt is omitted.

For example, the half gantry 3C is so formed that a cross section orthogonal to the rotation axis AX is substantially in a C shape and an opening parallel to the rotation axis provides an entrance 362. The treatment bed 6 causes the top plate 61 to move from the entrance 362 into the irradiation chamber 36 (a space that can be irradiated with a particle ray by the irradiation apparatus 5) and stops the top plate at a predetermined treatment location in the irradiation chamber 36.

When the top plate 61 is positioned in the irradiation chamber 36 in the half gantry 3C, the CT apparatus 7 waiting at an end of the half gantry 3C in the lengthwise direction moves to the irradiation chamber 36 and picks up an image of an affected part at an isocenter IC.

The thus configured present embodiment also brings about the same working-effects as First Embodiment does. The present embodiment can be combined with any of First to Third Embodiments. Further, the present embodiment is also applicable to any combination of First to Third Embodiments.

The present invention is not limited to the above-mentioned embodiments. Those skilled in the art can make various additions, modifications, or the like to the present invention without departing from the scope of the present invention. The above-mentioned embodiments are not limited to the configuration examples shown in the accompanying drawings. A configuration and a processing method of any embodiment may be appropriately modified to the extent that an object of the present invention is achieved.

For example, in the examples described above, the irradiation nozzle 53 is extended or restricted in three steps: the waiting position P1, the moving body tracking irradiation position P2, and the closest irradiation position P3. Instead, the irradiation nozzle 53 may also be extensible in two steps: the waiting position P1 and the moving body tracking irradiation position P2 or the waiting position P1 and the closest irradiation position P3. Further, the irradiation nozzle 53 may be extensible in four or more steps. In addition, the irradiation nozzle 53 may also be so configured that the irradiation nozzle is steplessly and continuously extended and restricted. In the examples described above, the irradiation apparatus 53 is fixed on the rotary gantry 3 or the half gantry 3C but a configuration in which the irradiation apparatus 53 is fixed on the building 10 without use of the rotary gantry 3 or the half gantry 3C may be also be adopted.

Each constituent element of the present invention may be arbitrarily added or omitted and an invention including an added or omitted constituent element is also included in the present invention. Further, a constituent element described in CLAIMS can be included in any other combination than those explicitly described in CLAIMS.

LIST OF REFERENCE SIGNS

1, 1B, 1C: Particle ray therapy apparatus
2: Particle ray generation apparatus
3, 3B, 3C: Rotary gantry
4: Beam transport system
5, 5A: Irradiation apparatus
6: Treatment bed
7: CT apparatus
8: Information processing system
35: Radiation therapy cage
36: Irradiation chamber
53, 53A: Irradiation nozzle

The invention claimed is:

1. A radiation therapy apparatus, comprising:
a treatment bed configured to move a top plate, with an object to be treated placed thereon, to a predetermined treatment location;
an imaging apparatus moving to the predetermined treatment location from a direction different from a direction of movement of the top plate, and picking up an image of the object to be treated;
an irradiation apparatus, that irradiates the object to be treated, provided between the treatment bed and the imaging apparatus, that is extendable and retractable in a direction of irradiation; and
a controller coupled to the imaging apparatus and the irradiation apparatus, the controller configured to:
control the irradiation apparatus to retract to a predetermined waiting position before the imaging apparatus moves to the predetermined treatment location,
control the irradiation apparatus to move to the predetermined treatment location while the irradiation apparatus is retracted, and
control the irradiation apparatus to extend to a predetermined irradiation position from the predetermined waiting position and apply a radioactive ray while in the predetermined irradiation position to the object to be treated,
wherein while the imaging apparatus is at the predetermined treatment location while the irradiation apparatus is retracted, at least a portion of the imaging apparatus is between the treatment bed and the irradiation apparatus in the direction of irradiation.

2. The radiation therapy apparatus according to claim 1, wherein the predetermined treatment location is within an imaging range of the imaging apparatus.

3. The radiation therapy apparatus according to claim 1, wherein the irradiation apparatus extends or retracts a nozzle portion applying the radioactive ray, thereby moving the nozzle portion between the predetermined waiting position and the predetermined irradiation position.

4. The radiation therapy apparatus according to claim 3, wherein the nozzle portion includes an extensible bellows pipe and equipment for monitoring and adjusting the radioactive ray, provided at a tip of the bellows pipe.

5. The radiation therapy apparatus according to claim 3, wherein the nozzle portion includes an unextensible single pipe and equipment for monitoring and adjusting the radioactive ray, provided on a tip side of the single pipe with a spacing in between, and movable between the predetermined waiting position and the predetermined irradiation position.

6. The radiation therapy apparatus according to claim 3, wherein the irradiation apparatus is configured to be moved to the waiting position at a predetermined angle.

7. The radiation therapy apparatus according to claim 6, wherein the predetermined angle is an angle at which the irradiation apparatus is positioned above the imaging apparatus.

8. The radiation therapy apparatus according to claim 1, further comprising:
a rotary gantry having the irradiation apparatus attached to the rotary gantry and revolving around the object to be treated,
wherein the treatment bed is positioned outside the rotary gantry and is capable of entering and exiting from the rotary gantry through an entrance to the rotary gantry, and
wherein the imaging apparatus is positioned at a back of the rotary gantry and is movably provided.

9. A radiation therapy apparatus, comprising:
a treatment bed configured to move a top plate with an object to be treated placed thereon to a predetermined treatment location;
an imaging apparatus configured to move to the predetermined treatment location from a direction of movement different from a direction of movement of the top plate, and pickup an image of the object to be treated at the predetermined treatment location;
an irradiation apparatus provided above the treatment bed and the imaging apparatus, that is extendable and retractable in a direction of irradiation, and configured to apply a radioactive ray to the object to be treated; and
a rotary gantry having the irradiation apparatus attached to the rotary gantry and revolving around the object to be treated,
wherein the irradiation apparatus retracts to a predetermined waiting position when the imaging apparatus moves to the predetermined treatment location, and moves to a predetermined irradiation position when applying the radioactive ray to the object to be treated, wherein the imaging apparatus is positioned outside the rotary gantry and is capable of entering and exiting from the rotary gantry through an entrance to the rotary gantry, wherein the treatment bed is positioned at a back of the rotary gantry and is movably provided, wherein while the imaging apparatus is at the predetermined treatment location while the irradiation apparatus is retracted, at least a portion of the imaging apparatus is between the treatment bed and the irradiation apparatus in the direction of irradiation.

10. A radiation therapy apparatus, comprising:

a treatment bed configured to move a top plate with an object to be treated placed thereon to a predetermined treatment location;

an imaging apparatus configured to move to the predetermined treatment location from a direction of movement different from a direction of movement of the top plate, and pickup an image of the object to be treated at the predetermined treatment location;

an irradiation apparatus provided above the treatment bed and the imaging apparatus, that is extendable and retractable in a direction of irradiation, and configured to apply a radioactive ray to the object to be treated; and a rotary gantry having the irradiation apparatus attached to the rotary gantry and revolving around the object to be treated, wherein the rotary gantry includes:
  a rotary barrel;
  a radiation therapy cage positioned inside the rotary barrel, revolving together with the rotary barrel, and forming the predetermined treatment location; and
  a stationary ring positioned inside the rotary barrel, revolving in an opposite direction to the rotary barrel, and forming a location of retraction of the imaging apparatus, wherein the irradiation apparatus retracts to a predetermined waiting position when the imaging apparatus moves to the predetermined treatment location, and moves to a predetermined irradiation position when applying the radioactive ray to the object to be treated, and wherein while the imaging apparatus is at the predetermined treatment location while the irradiation apparatus is retracted, at least a portion of the imaging apparatus is between the treatment bed and the irradiation apparatus in the direction of irradiation.

11. A radiation therapy apparatus, comprising:

a treatment bed configured to move a top plate with an object to be treated placed thereon to a predetermined treatment location;

an imaging apparatus configured to move to the predetermined treatment location from a direction of movement different from a direction of movement of the top plate, and pickup an image of the object to be treated at the predetermined treatment location;

an irradiation apparatus provided above the treatment bed and the imaging apparatus, that is extendable and retractable in a direction of irradiation and configured to apply a radioactive ray to the object to be treated, and a half gantry having the irradiation apparatus attached to the half gantry, the irradiation apparatus revolving around the object to be treated at an angle less than 360°, wherein the irradiation apparatus retracts to a predetermined waiting position when the imaging apparatus moves to the predetermined treatment location, and moves to a predetermined irradiation position when applying the radioactive ray to the object to be treated, wherein the imaging apparatus is positioned outside the half gantry in a rotation axis direction of the half gantry and is so provided that the imaging apparatus is capable of entering and exiting from the predetermined treatment location in the half gantry, wherein the treatment bed is capable of entering and exiting from the predetermined treatment location through an opening formed in a circumferential direction of the half gantry, and wherein while the imaging apparatus is at the predetermined treatment location while the irradiation apparatus is retracted, at least a portion of the imaging apparatus is between the treatment bed and the irradiation apparatus in the direction of irradiation.

12. A method for controlling a radiation therapy apparatus using a computer, wherein the radiation therapy apparatus includes:

a treatment bed configured to move a top plate, with an object to be treated placed thereon, to a predetermined treatment location;

an imaging apparatus moving to the predetermined treatment location from a direction different from a direction of movement of the top plate, and picking up an image of the object to be treated; and an irradiation apparatus, that irradiates the object to be treated, provided between the treatment bed and the imaging apparatus, that is extendable and retractable in a direction of irradiation, wherein the computer executes steps comprising:

instructing the treatment bed to move the top plate to the predetermined treatment location; instructing the irradiation apparatus to retract to a predetermined waiting position before the imaging apparatus moves to the predetermined treatment location;

instructing the imaging apparatus to move from a predetermined standby location to the predetermined treatment location while the irradiation apparatus is retracted such that at least a portion of the imaging apparatus is between the treatment bed and the irradiation apparatus in the direction of irradiation;

causing the imaging apparatus to pick up an image of an object to be diagnosed;

acquiring image data of the object to be diagnosed from the imaging apparatus, instructing the imaging apparatus to move from the predetermined treatment location to the predetermined standby location;

instructing the irradiation apparatus to extend to a predetermined irradiation position from the predetermined waiting position; and instructing the irradiation apparatus to apply a radioactive ray from the irradiation apparatus while in the predetermined irradiation position to the object to be treated in accordance with a treatment plan created based on the image data.

* * * * *